US007884196B2

(12) United States Patent
Lawless

(10) Patent No.: US 7,884,196 B2
(45) Date of Patent: Feb. 8, 2011

(54) VACCINE COMPOSITION COMPRISING METHYLATED DNA AND IMMUNOMODULATORY MOTIFS

(75) Inventor: Oliver Lawless, 6910 Deer Valley Rd., Highland, MD (US) 20777

(73) Assignee: Oliver Lawless, Olney, MD (US)

(*) Notice: Subject to any disclaimer, the term of this patent is extended or adjusted under 35 U.S.C. 154(b) by 155 days.

(21) Appl. No.: 11/244,142

(22) Filed: Oct. 6, 2005

(65) Prior Publication Data

US 2006/0111316 A1   May 25, 2006

Related U.S. Application Data

(60) Provisional application No. 60/615,937, filed on Oct. 6, 2004.

(51) Int. Cl.
    C07H 21/04   (2006.01)
    C12N 15/11   (2006.01)
(52) U.S. Cl. .................................. 536/23.1; 514/44
(58) Field of Classification Search .................. None
    See application file for complete search history.

(56) References Cited

U.S. PATENT DOCUMENTS

| | | | | | |
|---|---|---|---|---|---|
| 4,452,794 | A | * | 6/1984 | Kort et al. .................. | 514/179 |
| 5,955,443 | A | * | 9/1999 | Bennett et al. .............. | 514/44 |
| 6,008,344 | A | * | 12/1999 | Bennett et al. ............. | 536/24.5 |
| 6,447,765 | B1 | * | 9/2002 | Horwitz ..................... | 424/85.1 |
| 2001/0004456 | A1 | * | 6/2001 | Tobinick .................... | 424/85.1 |
| 2002/0064826 | A1 | * | 5/2002 | Ruben et al. ............... | 435/69.1 |
| 2005/0239733 | A1 | * | 10/2005 | Jurk et al. ................... | 514/44 |

OTHER PUBLICATIONS

Shuman et al. Journal of Biological Chemistry 1993, vol. 268, pp. 18943-18950.*
Kalota et al. Handbook of Experimental Pharmacology 2006, vol. 173, pp. 173-196.*
Sano et al. PNAS 1982, vol. 79, pp. 3584-3588.*
Chen et al. Gene Therapy 2001, vol. 8, pp. 1024-1032.*
Stacey et al. Journal of Immunology 2003, vol. 170, pp. 3614-3620.*
Gursel et al. Journal of Immunology 2003, vol. 171, pp. 1393-1400.*
Blass, "Immunologic Treatment of Alzheimer's Disease", Clinical Implications of Basic Research, vol. 341, No. 22, 1694-1695, Nov. 25, 1999, New England Journal Medicine.
Mitch Leslie, "Mindful of Metal"; http://sageke.sciencemag.org/cgi/content/full/sageke;, Mar. 26, 2003.
Saunders et al., "The role of apolipoprotein E in Alzheimer's disease: pharmacogenomic target selection", Biochimica et Biophysica Acta (BBA)/Molecular Basis of Disease 2000, 1502:85-94.
Checler et al., "Role of the proteasome in Alzheimer's disease", Biochimica et Biophysica Acta (BBA)/Molecular Basis of Disease 2000, 1502:133-138 Abstract.
Emmerling et al., "The role of complement in Alzheimer's disease pathology", Biochimica et Biophysica Acta (BBA)/Molecular Basis of Disease 2000, 1502:158-171.
Michael A. Boss, "Diagnostic approaches to Alzheimer's disease", Biochimica et Biophysica Acta (BBA)/Molecular Basis of Disease 2000, 1502:188-200.
Venters, et al., "A new concept in neurodegneneration: TNFα is a silencer of survival signals", Trends in Neurosciences, 2000, vol. 23, No. 4, pp. 175-180.
Rudd, et al., "Cbl sets the threshold for autoimmunity", Current Biology,2000, 10:R344-R347.
Daniel L. Mueller, "A proliferation of costimulatory molecules", Current Biology 2000, 10:R227-R230.
Hakon Heimer, "Outer causes of inner conflicts: Environment and Autoimmunity", Environmental Health Perspectives, vol. 107, No. 10, Oct. 1999.
Colin Watts, "Capture and Processing of Exogenous Antigens for Presentation on MHC Molecules", Annu. Rev. Immunol. 1997, vol. 15, pp. 821-850.
Taneja, et al., "Lessons from animal models for human autoimmune diseases", Nature Immunology, vol. 2, pp. 781-784, 2001.
Gregg J. Silverman, "B cell superantigens: possible roles in immunodeficiency and autoimmunity", Immunology, vol. 10, 1998, pp. 43-55.
Schmitt, et al., "Clinical Applications of Antineutrophil Cytoplasmic Antibody Testing", Curr Opin Rheumatol, vol. 16, No. 1, pp. 9-17, 2004.
Rogers, et al., "A Perspective on Inflammation in Alzheimer's Disease", Annals of the New York Academy of Sciences, vol. 924, pp. 132-135, (2000).
Janus, et al., "Transgenic mouse models of Alzheimer's disease", Biochimica et Biophysica Acta (BBA)/Molecular Basis of Disease 2000, 1502:63-75.
Golde, et al., "Biochemical detection of A$^\beta$isoforms: implications for pathogenesis, diagnosisi, and treatment of Alzheimer's disease", Biochimica et Biophysica Acta (BBA)/Molecular Basis of Disease 2000, 1502:172-187.
Akihiko Iwai, "Properties of NACP/α-synuclein and its role in Alzheimer's disease", Biochimica et Biophysica Acta (BBA)/Molecular Basis of Disease 2000, 1502:95-109—Abstract.
Haley, et al., "The Relationship of the Toxic Effects of Mecury to Exacerabation of the Medical Condition Classified as Alzheimer's Disease", http://www.alzforum.org/res/adh/hyp/mercury.asp, Aug. 13, 2001.
McGeer, et al., "Inflammation and the Degenerative Diseases of Aging" Annals NY Acad Sci, vol. 1035, pp. 104-116, (2004).

(Continued)

*Primary Examiner*—Tracy Vivlemore
(74) *Attorney, Agent, or Firm*—Pillsbury Winthrop Shaw Pittman, LLP

(57) ABSTRACT

The present invention relates generally to compositions and methods using mammalian, dsDNA (Double Stranded Deoxyribonucleic Acid) vaccination for the induction and maintenance of regulator suppressor T cells resulting in suppression of non infectious, and post infectious, inflammatory, allergic, auto-immune, vasculitic, certain degenerative vascular, and graft versus host diseases, with or without the use of IL-10, and with or without the use or TGFβ, with or without the use of anti-IL 6 receptor antibody, anti TNF antibody and or Plasmapheresis, IVIG, Corticosteroids, Methotrexate, Bromocriptine, and or vitamin D analogues.

7 Claims, 5 Drawing Sheets

OTHER PUBLICATIONS

Du, et al., "Association of an interleukin 1α polymorphism with Alzheimer's disease", Neurology, vol. 55, pp. 480-484, (2000)—Abstract.

Smith, et al., "Oxidative Stress in Alzheimer's disease", Biochemica et Biophysica Acta/Molecular Basis of Disease, vol. 1502, pp. 39-144, (2000).

SantaCruz, et al., "Tau Suppression in a Neurodegenerative Mouse Model Improves Memory Function", Science, vol. 309, pp. 476-481, (2005).

Clark et al., "CD40 and Its Ligand", Adv. Immunol., vol. 63, pp. 43-78, (1996).

Hathcock et al., "Role of the CD28-B7 Costimulatory Pathways in T Cell-Dependent B Cell Responses", Adv. Immunol.,vol. 62, pp. 131-166, (1996).

Tero Tapiola, "Biological Markers for Alzheimer's Disease", Doctoral Dissertation, ISBN 951-781-749-5, (2001).

Griem, et al., "Allergic and autoimmune reactions to xenobiotics: how do they arise?", Immunol. Today 19(3), pp. 133-141 (1998).

Pamela L. Schwartzberg, "Tampering with Immune System", Science 293 (5528): 228 (2001).

Syamal K. Datta, "Positive selection for autoimmunity", Nature Med., vol. 6, No. 3, pp. 259-261, Mar. 2000.

Davidson et al., "Autoimmune Diseases", Adv. Immunol. vol. 345, pp. 340-350, (2001), NEJM.

Blanco, et al., "Cytotoxic T Lymphocytes and Autoimmunity", CurrOpin Rheumatol., vol. 17, No. 6, pp. 731-734, (2005).

Rolf M. Zinkernagel, "Antiinfection Immunity and Autoimmunity", Annals of the New York Academy of Sciences, vol. 958, pp. 3-6, (2002).

John Hardy, "The Alzheimer family of diseases: Many etiologies, one pathogeneis?", Proc. Natl. Acad. Sci. USA: vol. 94, No. 6, pp. 2095-2097, (1997).

Jean Marx, "Preventing Alzheimer's: A Lifelong Commitment?", Science, vol. 309, Issue 5736, pp. 864-866, Aug. 5, 2005.

Koch, et al., "T-CIA: Investigating T Cells in Aging", Sci. Aging Knowl. Environ. vol. 2005, Issue 27, pp. pe21, Jul. 6, 2005.

Carina Treiber, "Metals on the Brain", Sci. Aging Knowledge, vol. 2005, Issue 36, pp. pe27, Sep. 7, 2005.

Tom Clarke, "Painkillers show Alzheimer's promise", http://www.nature.com/nsu/011108/011108-10.html.

Cooper et al., "Role of genetic Factos in autoimmune disease: implications for environmental research", Environ. Health Perspect, vol. 107, Suppl5, 1999, pp. 693-700—Abstract.

* cited by examiner

FIGURE 4

EFFECT OF CON-A OR DNA ON THE PHA RESPONSE OF NORMAL LYMPHOCYTES

| NO. | PRETREATMENT OF 48-Hr LYMPHOCYTES | CPMs | % INHIBITION |
|---|---|---|---|
| 1. | 0 | 23,009 | |
| | CON-A | 13,498 | 41 |
| | DNA | 15,939 | 30 |
| 2. | 0 | 34,678 | |
| | CON-A | 23,440 | 32 |
| | DNA | 25,570 | 26 |
| 3. | 0 | 36,601 | |
| | CON-A | 25,521 | 30 |
| | DNA | 29,370 | 20 |
| 4. | 0 | 9,750 | |
| | CON-A | 10,118 | +4 |
| | DNA | 7,468 | 23 |

SEQUENCE LISTING

```
<160> NUMBER OF SEQ ID NOS: 5

<210> SEQ ID NO 1
<211> LENGTH: 7
<212> TYPE: DNA
<213> ORGANISM: Bos sp.

<400> SEQUENCE: 1 ggagggg                                                                  7

<210> SEQ ID NO 2
<211> LENGTH: 6
<212> TYPE: DNA
<213> ORGANISM: Bos sp.

<400> SEQUENCE: 2
```

```
                                    -continued
ttaggg                                                                          6

<210> SEQ ID NO 3
<211> LENGTH: 6
<212> TYPE: DNA
<213> ORGANISM: Bos sp.

<400> SEQUENCE: 3 ctcgag                                                                          6

<210> SEQ ID NO 4
<211> LENGTH: 4
<212> TYPE: DNA
<213> ORGANISM: Bos sp.

<400> SEQUENCE: 4 ccgg                                                                            4

<210> SEQ ID NO 5
<211> LENGTH: 4
<212> TYPE: DNA
<213> ORGANISM: Bos sp.

<400> SEQUENCE: 5 tcga                                                                            4
```

VACCINE COMPOSITION COMPRISING METHYLATED DNA AND IMMUNOMODULATORY MOTIFS

PRIORITY

This application claims the benefit under 35 U.S.C. §119 (e) of provisional application 60/615,937, filed Oct. 6, 2004, the entire contents of which is specifically incorporated by reference for all purposes.

FIELD OF THE INVENTION

The present invention relates generally to compositions and methods using mammalian, dsDNA (Double Stranded Deoxyribonucleic Acid) vaccination for the induction and maintenance of regulator suppressor T cells resulting in suppression of non infectious, and post infectious, inflammatory, allergic, auto-immune, vasculitic, certain degenerative vascular, and graft versus host diseases, with or without the use of IL-10, and with or without the use or TGFβ, with or without the use of anti-IL 6 receptor antibody, anti TNF antibody and or Plasmapheresis, IVIG, Corticosteroids, Methotrexate, Bromocriptine, and or vitamin D analogues.

BACKGROUND OF THE INVENTION

The information provided below is not admitted to be prior art to the present invention, but is provided solely to assist the understanding of the reader.

Systemic Lupus versus local Autoimmune Diseases. Lupus is the prototypical disease of a generalized autoimmune dysfunction and immune dysregulation. Many of the diseases considered to be autoimmune have manifestations of local immune dysfunction only, as in Diabetes, Thyroid disease, Multiple Sclerosis, Crohns disease, Colitis, Ankylosing spondylitis, Psoriasis, gastritis caused by *Helicobacter pylori*, and the central nervous system disorders Alzheimers, ALS, and Parkinsons disease. Peripheral nerve-neuropathic disorders, skin disorders and generalized arteriosclerosis, affecting the coronary, cerebral, and peripheral arteries all have now been shown to be caused by locally induced chronic inflammation. They all show much less generalized immune dysregulation than that which is seen in Lupus.

Systemic Lupus-Autoimmunity Tolerance Immune Dys-regulation. Autoimmunity is considered to result and arise from the loss of Tolerance. Tolerance itself can be defined as the absence of an immune response to self and or other exogenous antigens. It can be ascribed to Innate, T and B cells and be manifested by failure of one or other of these individual cellular responses to the test antigens (which may be self or non self). It can also be due to loss of suppressor regulator T cells, both in number, and function. It can be central ie. arising from the thymus, or peripheral, involving peripheral T cells which fail to be anergized. Most available data on human Lupus (the prototype of a generalized autoimmune disease) and the equivalent mouse disease models, consider loss of anergy induction to be centered at the peripheral level. Suppressor T cell dysfunction has been associated with Lupus (Bresnihan and Jasin 1977; Horowitz, Borcherding et al. 1977; Morimoto 1978; Sagawa and Abdou 1978; Tardieu and Dupuy 1978; Kaufman and Bostwick 1979; Morimoto, Abe et al. 1979) (Abdou 1976, Krakower 1980) and both T cells and Monocytes have been shown to be important in this suppression. (Markenson, Lockshin et al. 1980) Furthermore anti T cell auto-antibodies and immune complexes have been implicated in loss of this T cell suppression, (Morimoto, Abe et al. 1979) which has been improved by, and following plasmapheresis. (Horwitz and Cousar 1975) When suppressor T cell function is lost there is an exaggerated B cell response to self antigens which results in a generalized autoimmunity as is seen in Lupus where antibodies are found to red cells, white cells, platelets, nucleic acids, nucleosomes, and other cellular components related to the apoptotic and necrotic cell death of T cells and Monocytes.

The immune system is essential for defending the organism against foreign invaders-bacteria, viruses, fungi and the like. It is generally assumed that the components of these offending agents or antigens are Non-Self, as distinct from self antigens such as dsDNA which has been shown to be critical in the etiology of Lupus and in particular the associated nephritis which arises from the deposition of immune complexes of dsDNA and anti DNA antibodies, in the kidneys of these patients. Most theories of Lupus etiology focus on genetic disturbances of T cell function (Tsokos 2003), and resultant T cell dysfunction. This T cell dysfunction or deficiency, in turn causes loss of T cell control of T cell dependent B cell function. The result is B cell clonal expansion and hyper-reactivity.

Another distinct and clearly different possibility which we here propose is that all self antigens preferentially induce central and peripheral Tolerance or immuno-suppression by activation of specific suppressor T cells and monocytes. Loss of this suppressor regulator T cell function which is central to this theory would predictably give rise to loss of self antigen Tolerance and result in antibodies and T cell responses to self antigens, and result in auto-antibodies, and T cell inflammation in organs, and auto-immune diseases. It is therefore responsible for the disturbed homeostasis and immune dysregulation which follows, which is central to Lupus pathogenesis, and to other allergic and autoimmune disorders. (Von Herrath et al. Nat Rev Immunol 223-232 2003).

Arthritis. This is caused by over 100 different diseases or disorders, and it affects over 70 million Americans. Rheumatoid Arthritis, Systemic Lupus Erythematosus, Scleroderma, Polymyositis, Mixed Connective Tissue Disease, Vasculitis affecting both large and small vessels, are all serious, potentially lethal, disabling diseases with high morbidity, high mortality, high dollar cost to the individual, the community, and the nation. They are all classified as Connective Tissue Disorders, or Disorders of persistent antigenic stimulation and result in Immune Dys-Regulation. Recent epidemiology data suggest that together they affect more than 30% of the US population, at a cost of over $12,000 per patient annually. All of these are considered to be of unknown cause or idiopathic, in nature. They are thus considered to be non infectious, and autoimmune, in that no identifiable organism has been identified as the primary cause of these illnesses.

Arterial-Degenerative Diseases.

Degenerative and inflammatory disorders involving the Coronary, Cerebral, and Peripheral arteries account for the greatest number of deaths annually in developed countries, and with increasing frequency the developing countries are following a similar pattern. Increasing evidence has been cited that inflammation in addition to high cholesterol, lack of diet and exercise, obesity and diabetes, play significant roles in causing this arterial degeneration. Thus cardiac C Reactive Protein CRP, has been identified as the highest risk factor for an acute coronary event in humans. This protein is produced by the liver in response to IL-6, and CRP is thus an inexpensive measure of IL-6. The annual cost in medical interventions, hospital costs, nursing home costs, insurance costs and disability costs have been estimated to be in the billions of dollars annually in the US alone. The precise cause of this inflammation is not yet clear but infections such as *Helicobacter, Chlamydia*, CMV, and others alone or by inducing heat shock proteins have been suggested. The latter have been shown to become auto antigens in CAD and Carotid artery disease. While the precise trigger of this inflammation is still to be determined, the presence of inflammation at the endothelial lining of the arteries is no longer disputed. (Ross R., N.E.J. Med. 1999 340:115-226).

The use of Statin drugs, and awareness of the role of diet and exercise, have for the first time begun to cause a reduction in the frequency of deaths and disability form these diseases, previously lethal at an early age. It has recently been shown that statin drugs, invented for their use as cholesterol lowering agents, are anti-inflammatory. They have even been shown to be efficacious in the treatment of Multiple Sclerosis, an inflammatory disorder of the brain caused by persistent immune activation. Statins may therefore influence disease patterns and outcomes by reducing inflammation as well as by lowering cholesterol levels.

Alzheimers disease. This is the single most important cause of dementia in developed countries where and when life expectancy has been increased. Recent statistics on this disease suggest that 1 in 4 or even more over 80 years of age will succumb to this disease. Over 20 studies have now shown that anti-inflammatory non steroidal aspirin like drugs, alter or suppress the progress of this disease. Amyloid fibrils, formed as result of cleavage of Amyloid Precursor Protein APP, by enzymatic cell membrane secretases, are formed from the $A\beta$ fragments produced by this cleavage. They are deposited in the brain at the synaptic clefts where acetylcholine ACH, and butyryl choline BCH, are produced and which are responsible for the transmission of the nerve impulses. Atrophy and loss of the neurons due to these amyloid proteins causing neural tangles, and Tau proteins causing neurofillament destruction, together with the major reductions of ACH and BCH levels on brain biopsies are considered the pathological and biological hallmarks of Alzheimers disease. Proinflammatory cytokines when measured in the brain tissues as messenger RNA, predate the finding of $A\beta$ in the brain. Chronic inflammation is thus an important mechanism in its causation.

The brain is a privileged site and evolved prior to the development of T cells and B cells. These cells should consequently never be seen within this privileged site, the brain, unless there is inflammation in it, or in the adjacent meninges or blood vessels. The more primitive innate immune cell system is represented here however by microglia and astroglia. Cells of the innate system in responding to antigens or triggers are known to produce the pro-inflammatory cytokines TNF-$\alpha$, IL-1, and IL-6. All three cytokines are found in and around the synaptic clefts at the site of deposition of the amyloid fibrils. Thus the finding of both amyloid fibrils and these Cytokines are evidence for persistent immune activation at the sites of neuronal damage, nerve cell atrophy or drop out, and ACH and BCH reductions. (McGeer & McGeer Science SAGE KE 2004 27: 29) Thus persistence of immune activation in response to as of yet some unknown trigger is the most likely cause of Alzheimers disease. No single method to abort the disease, or the deposition of amyloid and Tau proteins is currently available. All treatments are for symptoms only, where increase in ACH and BCH levels improve function temporarily.

Amyloidosis. This is a systematic disease caused by deposition Amyloid fibrils in organs and tissues such as spleen, liver, kidney and heart, in mammals including humans by persistent activation of the immune system. Diseases such as Tuberculosis, Osteomyelitis, and Leprosy, all of which are due to persistent infections, are frequently associated with systemic amyloidosis. This disease is uniformly fatal as no therapy has been identified to terminate the production of the amyloid proteins in the affected organs. Isolated organ death, or organ failure, is the usual cause of death in this disease. Organ grafting of kidney, heart, lung, liver, or bone marrow, is used, but the immunosuppressive regimens used to inhibit the GvH and HvG response to grafting may aggravate and accelerate the systemic amyloidogenic process, and thereby negate the effectiveness of the transplants. An effective method to reduce the chronic inflammation and immune activation is critically needed to treat this lethal disorder.

Organ Grafts and Disease. Organ grafting of kidney, heart, lung, pancreas, liver, bone marrow, stem cell, and bone marrow, are standard practice in the medical arsenal for responding to isolated organ failure, with a view to improving the quality and quantity of life, of the recipients. Organs other than autologous stem cell and bone marrow which are transplanted are obtained from unrelated donors, (allogeneic). As such there are genetic differences between the donors and the recipients. The resulting immune reactions which develop emanate from attempts by the recipient or the donor immune cells to immunologically reject the graft or the host cells. The former is termed host versus graft (HvG), and the latter graft versus host rejection (GvH), and disease. Allogeneic organ grafts and the HvG immune responses have been successfully controlled by the use of immune-suppressants. Because stem cell and bone marrow grafts include pluripotent immune cell progenitors there is a major need to alter the frequency and severity of the GvH disease resulting from allogeneic stem cell and bone marrow transplants. Successful intervention to prevent this GvH disease by acquiring Tolerance (Billingham Brent and Medawar Nature 1953 172; 603-606), would alter the underlying approaches to the treatment of Bone Marrow failure, spontaneously developing, or induced, and in the treatment of cancers of multiple types, and resistant autoimmune diseases, where bone marrow failure is the unwanted outcome of aggressive chemotherapy to alter immunity and kill the cancer cells.

Autoimmunity and Autoimmune Disorders and Diseases. Autoimmunity is defined as persistent and progressive immune reactions to non infectious self antigens, as distinct from infectious non self antigens from bacterial, viral, fungal, or parasitic organisms which invade and persist within mammals and humans. (Janeway 1992, & 1999).

The development of the newer biologics, in the form of monoclonal antibodies against the pro-inflammatory cytokines IL-1, TNF$\alpha$, IL-6, and IL-1 receptor, and their use in Rheumatoid Arthritis, Psoriasis, Crohns Disease, Colitis, and Ankylosing Spondylitis has resulted in major benefits characterized as clinical remissions or reductions in inflammation when monitored by ACR 20, ACR 50, and ACR 70 outcome responses; reduction in bony erosions on X Ray analysis, and in the prevention or reduction in deformities and disability. These improved outcomes have been major treatment advances allowing patients to reduce or eliminate the use of corticosteroids and some chemotherapy drugs which had previously been the standard of care for these diseases. These major advances have also revolutionized our understanding of the mechanism of these diseases. This excitement has been somewhat tempered by the development of bacterial infections, fungal and TB infections, in some patients, and in small numbers of reported deaths from cancer, both lymphoid and non lymphoid malignancies. These latter responses at this time are not statistically significant however. Nevertheless they are of concern in that they may increase in frequency as the duration of the use of these biologics increases. Gradual increase in dose requirements in order to maintain remission (Remicade), the development of antibodies against the biologic (Remicade), skin reactions (Enbrel and Kineret), the development of autoantibodies, vasculitis, and illnesses as are seen frequently in Lupus, are further complications which may limit the use of these biologics in the future.

Even with the use of all of these treatments individually, and combined, clinical response failures do exist, and have been cited as high as 50%. (Firestein 2003) Recourse then to plasmapheresis, and immunoadsorbent columns to remove inflammatory molecules, and to autologous and allogeneic bone marrow and or stem cell transplants, or to monoclonal antibodies against B cells and or the co-stimulatory molecules are the last resort for maintaining a pain free quality of life in this small group of response failures. The need for newer agents and treatments with out such complications or side effects is therefore apparent.

Background of CTdsDNA as an Immune Activator/Suppressor. Several hundred patents reviewed included the use of DNA as antigen vectors, immune enhancers, or adjuvants for vaccines. None of the patents already approved or pending identified CT DNA as an inducer of Suppressor/Regulator T cells, which then have the ability to suppress T cell and B cell stimulation and blastogenesis, to antigens, mitogens, and alloantigens.

Zeuner et al Arth &Rheum 2003, identified both immunostimualtory and immune suppressive oligodeoxynucleotides (ODNs) in mice. They suggested the use of suppressive ODNs may be useful in the prevention and treatment of proinflammatory diseases.

Zhao et al Antisense Nuceic Acid Drug Dev 2000 identified ODNs with CpG motifs as both neutral non stimulating and stimulatory introducing the idea that all CpG motifs were not stimulatory.

Mammone et al. Skin Pharmacol Appl Skin Physiol 2002. identified that UVL light induces damage to skin keratinocytes. They found that the trigger for repair was damaged DNA itself. They found that fragmented CT DNA irradiated and damaged with UVC light, caused a protective effect on the cultured keratinocytes. It caused a suppression of DNA synthesis in vitro thereby allowing repair. This effect was also dose dependent. The mechanism for this suppression was considered to be the p53 suppressor gene activation.

Yasuda et al Biochem Biphys Res Commun 2002 identified that naked CpG induced TNFα secretion from macrophages in vitro but DNA without CpG did not.

Wu et al PNAS 2002. Found that nonobese diabetic mice (NOD) have a deficiency of CD4 CD25 T cells in thymus and spleen. They suggest that a deficiency of Treg cells is responsible for diabetes induction and that as anti TNF neonatally administered prevents the disease, TNF in the thymus may have a role in disease induction. (IL-6 was not measured however in the study).

Bresnihan, B. and H. E. Jasin (1977). "Suppressor function of peripheral blood mononuclear cells in normal individuals and in patients with systemic lupus erythematosus." J Clin Invest 59(1): 106-16. Normal peripheral blood mononuclear cells demonstrated increased DNA synthesis and secretion of newly synthesized protein when suboptimal concentrations of Concanavalin A (Con A) were added to the cultures after 24-h incubation in vitro. Cells stimulated by Con A, 1 mug/ml, after 24-h incubation demonstrated 3.0 times more tritiated thymidine incorporation, and 4.4 times more 14C-amino acid incorporation into newly synthesized secreted protein, than cells stimulated at 0 h (P less than 0.001). The acquisition of increased responsiveness was not abrogated by washing and resuspending the cells in fresh medium. Since the increased responsiveness could be inhibited by the addition to the cultures of small numbers of cells previously activated by Con A it is suggested that the enhanced reactivity acquired in culture represents the loss of a subpopulation of suppressor cells that modulate the T-lymphocyte response. Cells from nine patients with active, untreated systemic lupus erythematosus demonstrated normal responses to optimal concentrations of Con A added at 0 h, but an impaired response to Con A, 1 mug/ml. When these cells were incubated for 24 h, a significant increased response to Con A was not observed. This observation suggests that patients with active SLE lack circulating suppressor cells. When seven SLE patients were again studied after corticosteroid therapy had led to clinical improvement, the response to Con A, 1 mug/ml, added after 24-h incubation was similar to that observed in normal controls, suggesting that suppressor function in SLE returns as disease activity declines.

(Aldo-Benson 1989) found that B cell clones from both autoimmune disease (AID) prone and non AID prone mice could be maintained in culture and that added dsDNA induced T cells to the cultures suppressed the B cell clones in the non AID prone but not in the AID prone.

(Ochi, 1983 #258) found that procaine amide enhanced autoantibody production and AID in prone mice by altering suppressor T cell induction. (This drug is now known to demethylate CpGs, which may be the mechanism).

(Newman, 1979 #218) showed a lack of Ts suppressor T cells in Lupus. (Miller, 1989 #437) identified a thymic factor TsIF which was produced from thymic epithelial cells co-cultured with T cells and which upon injection could suppress Lupus and Rheumatoid arthritis inflammation in AID prone mice. The data suggests a soluble factor from thymus can induce T cell suppression.

Horowitz, S., W. Borcherding, et al. (1977). "Induction of suppressor T cells in systemic lupus erythematosus by thymosin and cultured thymic epithelium." Science 197(4307): 999-1001.

(Blank, 1991 #192) showed dsDNA specificity to the induction of Ts cells in suppression of B cell autoantibody production.

(Borel, 1980 #177) was the first to show nucleic acid specific induced B cell suppression and considered it a potential method of treatment for AID.

(Chen, 2001 #935) in an effort to understand the differences in DNA sources as immune activators/suppressors found that *E coli* (EC) DNA was an immune inducer while calf thymus DNA (CT DNA) was an immuno-suppressor. The former contains CpG motifs which are unmethylated, and which are not found in CT DNA. The mechanism for EC stimulation was different from but synergistic with Endotoxin. The mechanism for immunosuppression was considered to be due to inhibition of the EC induced signaling by NFkappa-B and AP-1. (It is now known that EC CpG motifs activate TLR 9 (O'Neill 2003) and endotoxin TLR 4, and the fact that dsCTDNA suppresses EC but not endotoxin suggests the silencing of activation may be through TLR 9 or its adapter proteins, or transcription factors).

(Schwartz, 1997 #879) showed that EC DNA with CpG motifs activate inflammation in the lungs also.

(Segura-Pacheco, 2003 #1) in an interesting study showed that the drug hydralazine—a known inducer of Lupus in man de-methylates DNA. Because activation of suppressor T cells is known to be associated with certain cancers, they suggested that the use of this drug may alter the suppressor T cell state found in cancer, by re-initiating immune activation by DNA de-methylation.

Circulating DNA has been reported in the plasma of patients with different cancers, aging, pregnancy and other states. It may therefore play a significant role in the immunosuppression associated with both pregnancy and certain cancers. Suggestions for the use of immunostimulatory DNA with unmethylated CpG motifs to upregulate DCs, CD 4 and CD 8 to kill cancer cells have accordingly been entertained.

Other objects and advantages will become apparent from the following disclosure.

SUMMARY OF THE INVENTION

An aspect of the present invention provides pharmaceutical compositions for administration as vaccines to mammals. According to an aspect the pharmaceutical compositions comprise DNA. According to an aspect the DNA is double-stranded (ds). According to an aspect the DNA has an average molecular weight of from about 10 k to about 50 k Daltons.

According to an aspect, the DNA is methylated. According to a preferred aspect, the DNA is methylated by a mammal, in vivo. The DNA may be methylated prior to extraction from the cells of a mammal. According to a preferred aspect the DNA is isolated and purified from calf thymus.

According to alternative preferred aspects, the DNA is methylated, in vitro. In vitro methylation may be catalyzed enzymatically by enzymes such as, but not limited to, DNA methyltransferase 1 (Dnmt1), Dnmt3a, and/or Dnmt3b. According to an aspect, the DNA is isolated and purified from a biological source prior to methylation in vitro.

According to an aspect the pharmaceutical composition may further comprise at least one agent selected from cytokines such as IL-10 and/or TGF.beta., antibodies such as anti-IL 6 receptor antibody, anti TNF antibody and/or immune globulin (IG); anti-TNF.alpha. biologics such as, but not limited to, ENBREL® (etanercept), REMICADE ® (Infliximab), and or HUMIRA® (adalimumab); or an immunosuppressive agent such as, but not limited to, Corticosteroids, Methotrexate, Bromocriptine, and or vitamin D analogues.

According to an aspect, the invention provides methods for treating inflammatory, non infectious and/or post infectious, allergic, autoimmune, vasculitic, degenerative vascular, host v graft, graft v host diseases, Alzheimer's Disease, and amyloidosis by administering to a mammal a pharmaceutical composition comprising DNA. According to an aspect the DNA is double-stranded (ds). According to an aspect the DNA has an average molecular weight of from about 10 k to about 50 k Daltons.

According to an aspect of the method, the DNA is methylated. According to a preferred aspect, the DNA is methylated by a mammal, in vivo. The DNA may be methylated prior to extraction from the cells of a mammal. According to a preferred aspect the DNA is isolated and purified from calf thymus.

According to alternative preferred aspects of the method, the DNA is methylated, in vitro. In vitro methylation may be catalyzed enzymatically by enzymes such as, but not limited to, DNA methyltransferase 1 (Dnmt1), Dnmt3a, and/or Dnmt3b. According to an aspect, In vitro methylation is achieved through non-enzymatic means. According to an aspect, the DNA is isolated and purified from a biological source prior to methylation in vitro.

According to an aspect, the pharmaceutical composition administered as part of the method may further comprise at least one agent selected from cytokines such as IL-10 and/or TGF.beta., antibodies such as anti-IL 6 receptor antibody, anti TNF antibody and/or immune globulin (IG); anti-TNF.alpha. biologics such as, but not limited to, ENBREL® (etanercept), REMICADE® (Infliximab), and or HUMIRA® (adalimumab); or an immunosuppressive agent, such as, but not limited to Corticosteroids, Methotrexate, Bromocriptine, Immuran CellCept® (mycophenolate mofetil), and or vitamin D analogues.

According to additional aspects, one or more additional agents may be administered separately from the DNA vaccine. The additional agent may be one or more of a cytokine, such as IL-10 and/or TGF.beta.; antibodies, such as anti-IL 6 receptor antibody, anti TNF antibody and/or immune globulin (IG); anti-TNF.alpha. biologics such as, but not limited to, ENBREL® (etanercept), REMICADE (Infliximab), and or HUMIRA® (adalimumab); or an immunosuppressive agent, such as, but not limited to, Corticosteroids, Methotrexate, Bromocriptine, Immuran CellCept® (mycophenolate mofetil), and or vitamin D analogues.

According to an aspect, the method further comprises treatment of the mammal by a technique such as plasmapheresis and/or intra venous administration of immune globulin (IVIG).

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 4: Normal PBMs were incubated with CT DNA, or CON A, for 48 Hr, washed and then reincubated with fresh PBMs in the presence of PHA. Results show significant reductions in CPMs of normal cells in response to PHA in the presence of 48 hr PBMs pretreated with either Con A or DS DNA.

DETAILED DESCRIPTION OF A PREFERRED EMBODIMENT

Figure 1:
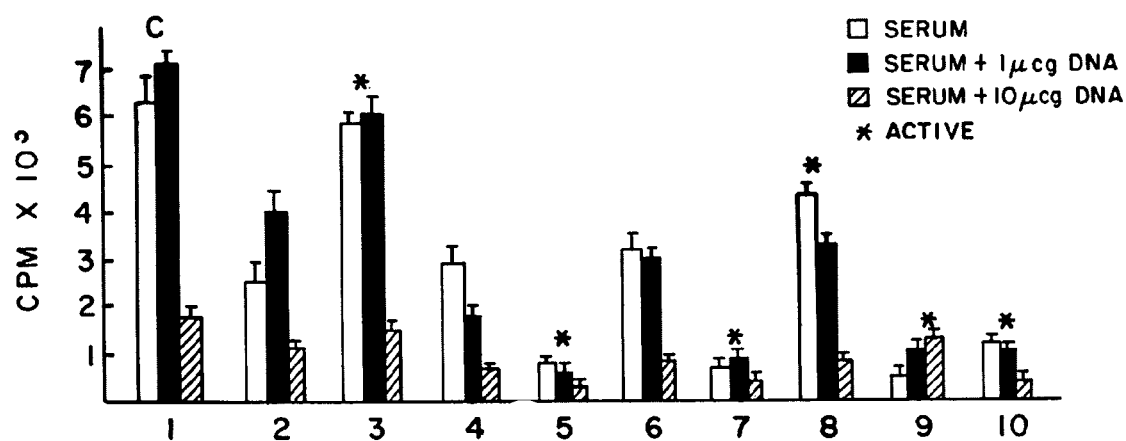
FIG. 1: CPMs of normal C, and 9 Lupus-2-10, patients to SK SD in the presence of normal serum, serum with 1 and 10 μcg of CT DNA. The * denotes active disease. Results show that in normal-C, and Lupus PBMs 2-10, in normal serum, the addition of 1 and 10 μcg CT dsDNA suppresses the SK SD response in normal PBMs, and in both active and inactive Lupus patients.
Figure 2:
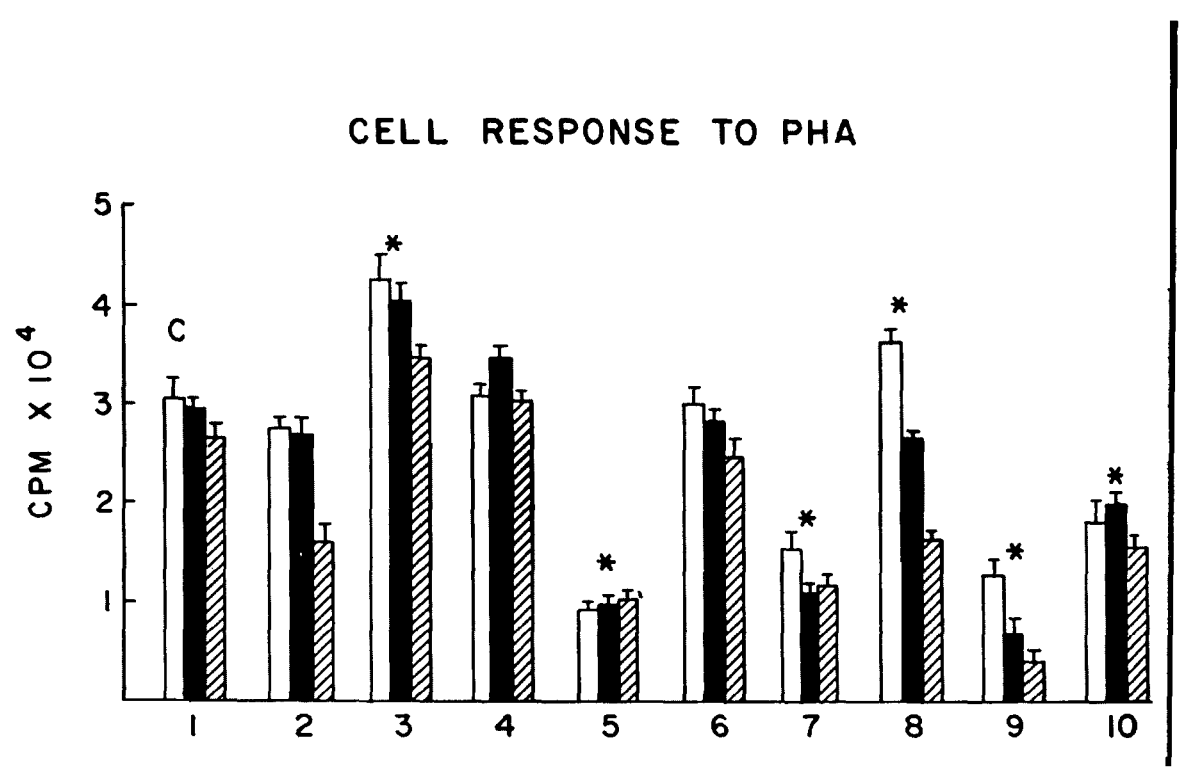
FIG. 2: CPMs of normal C, and 9 Lupus 2-10, patients to PHA in the presence of normal serum, serum with 1 and 10 μcg of CT DNA. The * denotes active disease.
Figure 3:
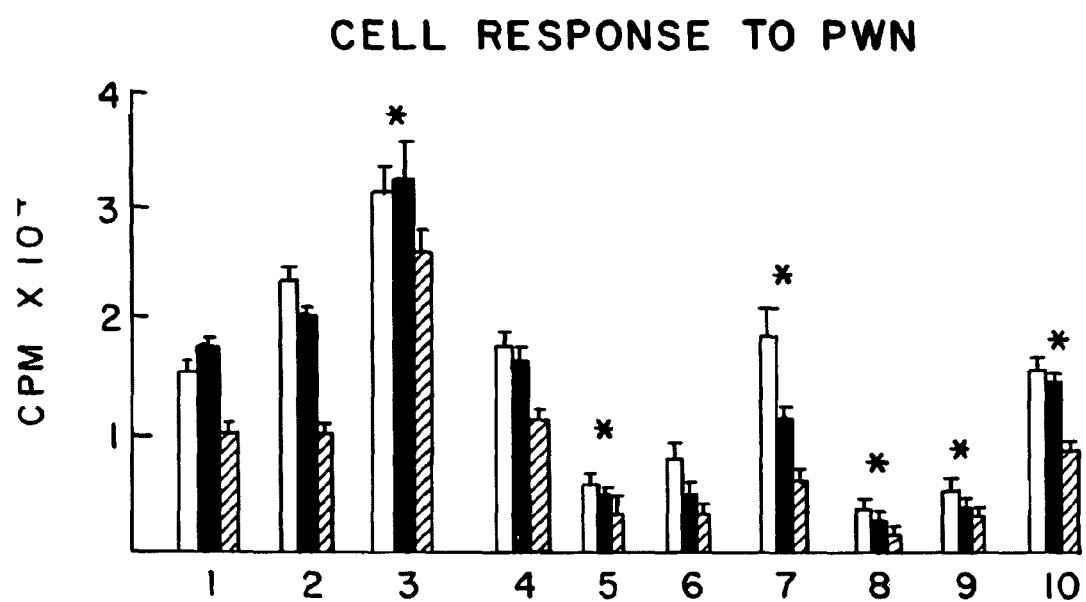
FIG. 3: CPMs of normal C, and 9 Lupus-2-9, patients to PWM in the presence of normal serum, serum with 1 and 10 μcg of CT DNA. The * denotes active disease. Results show reduction of PWM responses in normal and in Lupus patients with 1 and 10 μg of CT DNA. The * denotes active disease. The degree of suppression is greatest with the higher dose of DS DNA.
Figure 5:
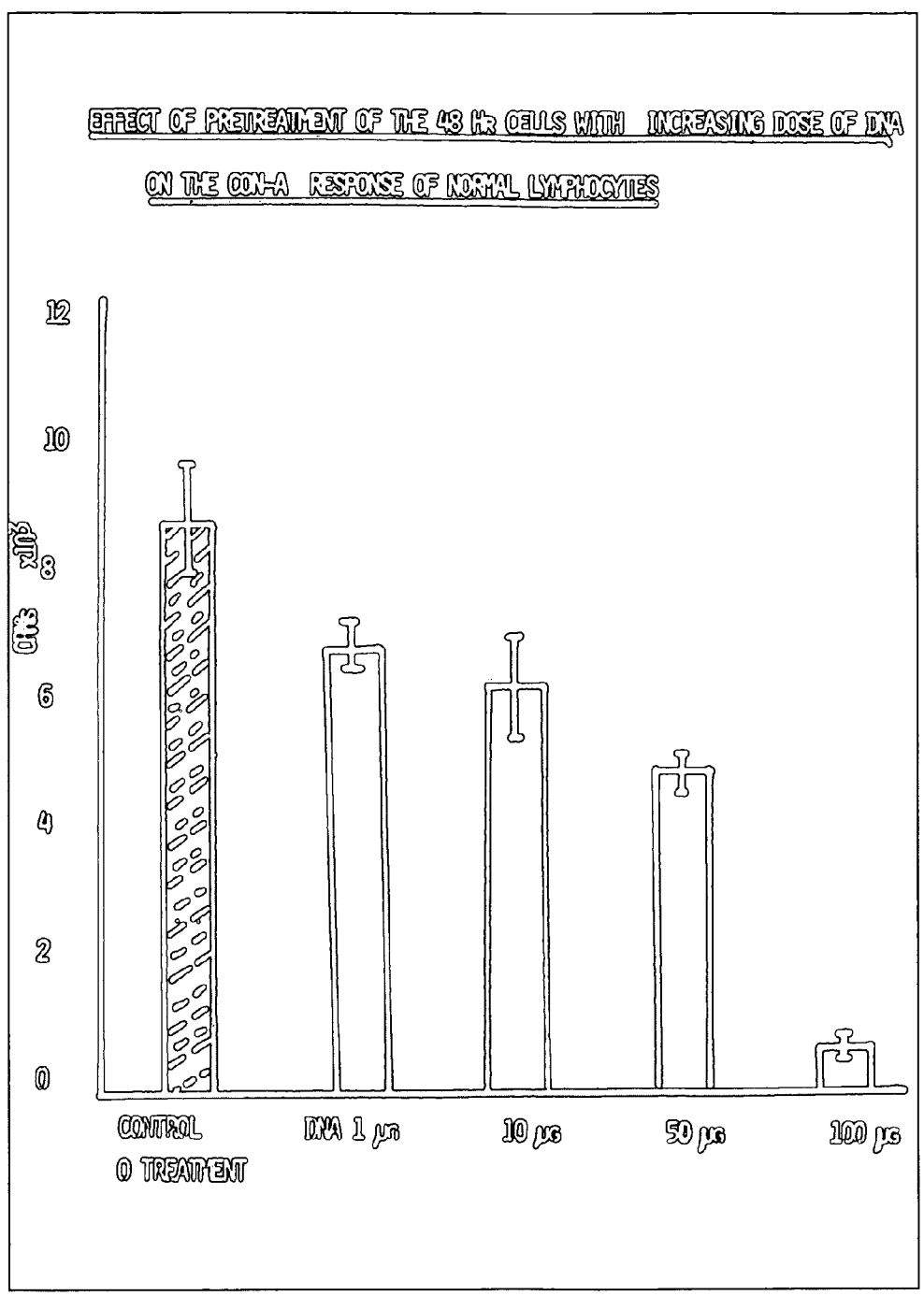
FIG. 5: CPMs of normal cells in response to Con A in the presence of 48 hr pre-incubated cells pretreated with increasing doses of dsDNA from 1-100 μcg. Results show a linear decrease in CPMs of normal cells in response to Con A with increasing doses of DS DNA.

Reference is made to the figures to illustrate selected embodiments and preferred modes of carrying out the invention. It is to be understood that the invention is not hereby limited to those aspects depicted in the figures. The advantages of the invention relate to easy availability, manufacture and production, ease of administration, low cost, potential avoidance of toxic drugs including steroids, and chemotherapy agents, and the newer biologics with their attendant complications and their cost, methods of functional assessment of response, and monitoring of efficacy by measuring CD4+ CD 25+ Regulator/Suppressor T cells. Cost of the currently used biologics averages $3-5000 monthly. While it may be necessary to use these biologics it is expected that they will be needed on a one time or transient basis only. Likewise once homeostasis has returned and inflammation is controlled, the need for continuous use may be abrogated unlike the anti TNFs which need to be administered continuously- weekly, biweekly, or monthly-indefinitely.

Use of an natural agent dsDNA obtained from the mammalian, preferably human, and autologous source which can induce suppressor and regulator immune T cell function in patients with illnesses related to persistent non infectious inflammatory disorders affecting individual organs, immune dysregulation, vascular degeneration, autoimmunity, vasculitis, graft versus host disease, host versus graft disease, Alzheimers disease, Amyloidosis, and hyper-immunity is the main embodiment of this discovery. The embodiment can be used in a suppression induction regime, and in a maintenance regime, with and without the use of plasmapheresis, & IVIG, with and without the use of bromocriptine, and vitamin D, with and without the use of IL-10, and TGFβ, with and without the use of anti IL-6 receptor antibody, with and without the use of anti TNF alpha receptor monoclonal antibodies such as Enbrel/Etanercept, and the TNF alpha monoclonal antibodies such as Remicade/Infliximab and or Humira/Adalumibab.

Normal Immune Response. In mammals including humans the immune response to an infectious agent or toxin is characterized by clonal expansion of the T or B cell population specific for the inciting organism, antigen or agent. (Burnet 1995) This immune responsiveness results in killing of the organism, cytolysis of the invading cells, neutralization of the toxins, and eventual elimination of the foreign body from the host. Following the elimination of the toxic invader the expanded T and B cell clones have to regress to their baseline homeostatic state by a process of activated immune cell death (AICD). Failure of regression, or continued cell growth of these immune cells by failure of naturally occurring death by apoptosis, or of suppressing cells and factors would theoretically lead to uninhibited T and B cell growth, and result in T cell lymphomas and Leukemias, B cell Lymphomas, Mutiple Myeloma or Waldenstroms Macroglobulinemia. All of these have been reported to develop spontaneously in the primary connective tissue disease, and may be further increased with the use of chemotherapy agents. The proinflammatory cytokines IL-1, IL-6, and TNFα are all important in maintaining this state of immune homeostasis. Tumor necrosis factor was so named because of its ability to "kill tumors". Inadequate TNFα production, or its suppression by biologics may thus theoretically lead to lymphoid, and even other malignancies.

Genes and Environment. All of the diseases cited already are considered to be auto-immune in their causation and genesis. Genetic susceptibility as well as environmental agents are considered to be critically important in both their initiation and their persistence. Failure to regain immune homeostasis, immune dysregulation, and persistent triggering by antigens or adjuvants, are all potential mechanisms for causing persistence of these diseases.

Environment and Genes. It makes biological and evolutionary sense that self antigens be non immunogenic. Self antigens in the presence of persistent environmental chemicals which can be shown to be pro-inflammatory in that they cause the production of IL-1, IL-6, and TNF alpha could make non immunogenic self antigens become immunogenic. Chemical induced apoptotic and necrotic cell death have been identified in Lupus and Scleroderma (Casciola and Rosen 1994, 1997 & Andrade et al 2000) as the source of these self antigens, which then become immunogenic. A recent epidemiological study in the Carolinas has shown a greater than 4 fold enhanced relative risk for development of Lupus in those exposed to the highest ambient silica exposures. Silica is a potent and persistent activator of IL-1, IL-6 and TNF alpha. It also causes apoptosis and necrosis. It persists in the body after exposures. In occupationally exposed silicosis patients it causes hyper-immunity, T cell dysfunction and autoimmunity. Other drugs and chemicals cause drug induced Lupus, and once they are removed or withdrawn the disease stops. Thus there is precedence for thinking that Lupus has an acquired environmental component in addition to, a solely genetic disorder affecting T cells.

Lupus—Breaking of Tolerance versus Suppressor/Regulator T cell dysfunction. Lupus is caused by induced antibodies and T cells to nuclear self antigens—ANA, DNA, Sm, RNA, RNP and others, which are deposited in tissues throughout the body where they cause inflammation-arthritis, dermatitis, nephritis etc. Low levels of antinuclear antibodies are detected in normals, following infections, vaccinations, certain drugs, and in the elderly, suggesting that both non self, altered self, as well as self antigens invoke both antibodies and autoantibodies.

Certain drugs and environmental chemicals, cause Lupus, which abates, and frequently enters remission, with the drug withdrawal. Lupus can be active, inactive, acute, chronic, remit spontaneously or following drug treatments, or be persistent and progressive.

Immune system testing and function in Lupus is dependent on the number, severity, and distribution of the symptoms present at the time of testing. The presence of auto-antibodies does not define the presence of inflammation. Auto-Antibodies are almost always present in the presence of inflammation. When antibody levels are high and the patient is in a flair, with active symptoms, serum complement proteins C 3, C 4, and CH 50, are frequently low. (Lloyd & Schur Medicine 1981 60.208).

Deficiency in number and function of T cells is found in association with active Lupus. (In this regard it resembles HIV disease). Clonal expansion of B cells producing antinuclear, and other self auto-antibodies usually of the IgG class, frequently complexed with DNA in the form of high molecular weight immune complexes, are found deposited in the kidneys, also in the circulating plasma, and are the hallmark of Lupus. (Akashi 1995). Antibodies to T cells are found in active Lupus, and their role in T cell dysfunction is unclear, and even may result in T reg dysfunction (Bi 1990). T cell dysfunction co-exists with and may be responsible for the B cell hyper-production of auto-antibodies. (Kammer 1983).

Active Lupus patients are immuno-supressed, ie. They are susceptible to outside infections-due to the disease itself and or the treatments. (Another analogy with AIDS).

Recent information has identified the importance of the gene Foxpro3 which is induced by thymus epithelium to cause T cells to develop CD25+ CD4+ (TReg,) or regulator T cells, in animal models of autoimmune diseases. Deficiency of this gene leads to wide spread autoimmune phenomena and diseases. Re-Insertion of this gene corrects the anomalies. This finding further emphasizes the importance of these regulator T cells and the need for a method for their induction in prevention and control of autoimmunity. Reduction in both number and function of these cells have now been reported in animals and humans in both localized autoimmune diseases such as Autoimmune Polyendocrinopathy syndromes, Type I diabetes mellitus (TIDM), autoimmune gastritis, colitis, and thyroiditis, as well as in the generalized autoimmune diseases typified by human Lupus, and the animal-models of Lupus-NZB NZW F1 hybrid mice that have been the most widely used and the greatest benefit to our current understanding of the human disease. This natural suppression tends to be reduced or abrogated in these localized and generalized autoimmune diseases. It is also reduced in aging, where auto-antibodies and autoimmune disorders are increased in prevalence, and in Alzheimers disease, and now also in HIV AIDS. The cytokine which has been most important in overriding or breaking this immune-suppression is IL-6. (Pasare and Medzhtivov et al Science 2003) Generation, development, and function of TReg cells is dependent on upregulation of MHC II and co-stimulatory molecules on DCs. (see below) However diseases such as Lupus are complicated by major changes in cytokine, antibody, complement, immune complex levels, and the avidity of the antibodies formed at different stages of the disease and at different degrees of disease activity. Furthermore phagocyte dysfunction, T cell dysfunction, and dysfunction of immune complex clearance and inadequate apoptosis and clearance of apoptotic cells, and cell necrosis, are all variables which are altered by disease activity and which need to be assessed in regard to the timing of use of the embodiment for induction of TReg cells. Thus plasmapheresis, anti-IL-6R antibody, IL-10, TGFβ, may need to be administered prior to or coterminous with the use of the embodiment, based upon the initial clinical and immunological findings in each individual patient.

Immune Perspectives. Several important immune tenets merit reflection here. In the broadest sense, the primary goal of the mammalian immune system is to preserve homeostasis within the organism. The natural state of the system is flux, a feedback continuum, with continual destruction and regeneration at the cellular level. A result of this defining state is that every action must be able to obtain a reaction to continue trending toward homeostasis. The system's composition, as well as the resources it has at its disposable for defense may also be deemed "natural": capable of being organically destroyed and regenerated. The organism's composition and adaptability, as well as that of its constituent parts, is physically limited only by its genetically coded building blocks (DNA and proteins) and capabilities, which it has attained over the course of its evolution. The system is self-contained and inter-dependent, and when posed with a threat, focuses on containment, since deviations in one area may affect the function of other areas. Finally, the immune system, as well as it's individual components, such as organs and tissues, operate with the functional goal-oriented aim of trending back to homeostasis. The mammalian immune system, an evolutionary marvel, is a continuum, limited only by the evolutionary tenets which it is based on. The significance of these elementary tenets is that there are degrees wherein violation does not result in organic death, but will serve to severely disrupt and impair immune function, at first locally, and then systemcally. Local containment is therefore preferable to systemic disease.

Conventional Immune Theory. Historically, the innate/non-specific and adaptive/specific immune systems have been treated as separate functional entities, with independent roles and resources. Investigation of the innate system has been largely neglected due its limited complexity, resources, and role in an immunogenic response. However, regardless of the simplicity and limitations of its cellular components, it maintains a paramount role in communication between the two cellular systems and in initiation and coordination of an efficient adaptive immune response.

Innate Immunity. The innate/non-specific immune system is the evolutionarily older system, and is found in both invertebrates and vertebrates. In a simplistic sense, the innate immune system provides an initial non-antigen-specific response to a foreign substance, which upon subsequent encounter with the same substance, merely repeats the same general response (Bellanti, 49). Its primary cellular components are macrophages, dendritic cells ("DCs"), natural killer cells ("NKs"), and T cells. The functional simplicity of these component cells enables rapid response kinetics. Macrophages and DCs recognize repetitive molecular patterns, or pathogen-associated molecular patterns ("PAMPs") on their pattern recognition receptors ("PRRs"). All of their PRRs were said to have the same specificities. (see below) As a result, phagocytes and DCs have a limited number of pre-existing cell types and responses. The adaptive/specific immune system, found only in vertebrates, is more discriminatory, and may be characteristically distinguished from the innate system through its specificity, heterogeneity, and memory upon subsequent antigenic encounters (Bellanti, 49). All three adjectives describe the increasingly complex roles played by lymphocytes such as T cells and B cells, which can selectively proliferate and differentiate themselves upon subsequent exposures to antigens.

The macrophage plays a central role at the innate/non-specific level. It serves a dual function, which is fundamentally different at different times. In its basal state, macrophage function is centered on homeostatic functions such as the phagocytosis of proteins and apoptotic cells and debris. However, it also functions as the first line of immunological defense and becomes activated in response to external threats. Much of the destructive capacity of the immune system, with respect to tissue damage, is invested in macrophages. The activated phenotype is histotoxic, with a potent ability to initiate adaptive immunity and capacity to kill cells and organisms and to catabolize or destroy antigen(s) or PAMPs. As a consequence, the role of the activated macrophage under "normal" conditions is limited in terms of specificity and duration. The critical difference in its functional efficacy is its ability to initiate inflammation. During activation, following receptor triggering, signalling transduction gives rise to altered gene expression, coordinated and controlled production of effector and inhibitory cytokines, extracellular proteinases. Cell-bound ligands, and microbial products leads to temporary production of the proinflammatory cytokines TNFα, IL-1, IL-6, IFNα, and IFNγ ((Nathan and Muller, 2001). The activated macrophage produces these macrophage derived interleukins ("MDI") in staggered intervals over a four hour time cycle which serve to degrade the causative agent, alter chemokine migratory patterns, and activate and differentiate cells associated with the response.

The macrophage's response to the two forms of cell death has been shown to be rather important, since the induction of inflammation brings with it numerous secondary consequences. It has been shown that cellular apoptosis does not initiate an macrophage-based inflammatory response, and in fact may be inflammatory suppressive (Cocco and Ucker, 2001). Cellular apoptosis is characterized by an orderly sequence of internal events. Chromatin condensation precedes the loss of cellular integrity, thus providing a means of containment for nuclear components (Russell, 1983; Wyllie et al, 1984; Harvey et al, 2000). As a consequence of this containment, bystander cells remain unaffected by intracellular processes (Ucker et al, 1989; Dhein et al, 1995). In contrast, necrotic cell death is characterized by rapid, disorganized swelling and rupture and is associated with pathological tissue injury (Henson and Johnson, 1987). The phagocytic response to necrotic cell death and foreign threats is marked by the initiation of inflammation (Henson and Johnson, 1987; Stern et al, 1996) for containment and elimination by itself and other cells attracted to the site by chemotaxis. It is now generally recognized that the inappropriate production of TNFα, IL-1 and IL-6 leads to continuous inflammation, tissue destruction and organ injury (Beutler and Cerami, 1986; Edwards et al, 1994; Ksontini et al, 1998). As such, an active program of cytokine mediated suppression is initiated upon containment and elimination of the causative agent. This suppression phase reorients the cell toward trophic functions such as wound healing tissue regeneration and repair. (Nathan and Muller, 2001). However, perceived macrophage failure such as the inability to kill or contain the causative agent will escalate the level and specificity of the immune response. Accordingly, the immune system transitions its defense from its non-specific to its specific mechanism of defense. The cellular protagonists which drive the specific arm of the immune defense are T cells and B cells, and the macrophage's role after this transition is largely ignored.

Adaptive Immunity. The adaptive/specific immune response is defined by the presence of clonally expanded antigen-specific T and/or B cells in response to a specific antigen. The 2 signal model is the currently accepted model for specific immune activation. It posits, obviously, that specific immune induction requires 2 signals. The cause of induction of the initiating signal is still under debate. A popular theory espoused by Matzinger is that danger in the form of tissue damage or cell stress triggers the response termed signal 1 (Matzinger, 1994). Signal 1 itself is an interaction involving antigenic protein/peptide transfer between the antigen-presenting cell ("APC") and either the T cell receptor ("TCR") on naive T cells or cell-membrane-bound immunoglobulins on B cells (Matzinger 1994). Activated macrophages or dendritic cells ("DCs") may function as APCs, although it has been shown that macrophages and immature DCs, are weak APCs, in comparison with mature DCs. Contact with proinflammatory cytokines, microbial products, or antigens induces DC maturation, characterized by expression of class I and II major histocompatibility complex ("MHC") molecules and costimulatory molecules such as CD80 and CD86 (Arend, 2001). These mature DCs present peptide antigens to CD4+ T cells via class II MHC complexes, to CD8+ T cells via class I MHC complexes, and potentially endogenous and exogenous lipids and glycolipids via molecules of the CD1 family (Arend, 2001). The addition of signal 2 consists of costimulatory molecules such as proinflammatory cytokines, CD2, CD58, CD40, CD40 ligand, CD28, B7, B7.1, B7.2, B7.3, CD58, LFA3, or adhesion molecules which assist in priming the CD4+/T helper cells (Arend 2001). When both signals are present, T cells clonally expand and differentiate, based on the milieu of surrounding cytokines.

A Th 1 response, involved in cell-mediated immunity and some auto-immune diseases, is manifested by delayed type hypersensitivity to the inducing antigen and produces the cytokines IL-2 and IF gamma and TNF (Mosman et al 1989). A Th 2 response, involved in humoral immunity, some auto-immune and allergic diseases, results in the production of IL-4, IL-5, IL-6, IL-10, and IL-12 (Mosman et al 1996). Failure to eliminate the antigen at the Th 1 lymphocyte cell level, or the cytokine milieu induced by the incriminating agent or antigen elicits Th 2 T cell activity, which in turn initiates B cell function (cite). B cell activation produces the antibodies IgG, IgM, IgA, IgD, and IgE, depending on the anatomical location of the antigen being presented. With time and antigen persistence, an initial IgM antibody switches to an IgG antibody and the avidity of this antibody increases progressively with the aim of complexing, precipitating, and localizing it for phagocytic removal. On occasion, a secondary antibody may be formed against this complex for the same purpose. This is an IgM anti IgG Antigen as complex which is also called Rheumatoid Factor (RF) which is found in Rheumatoid Arthritis and other chronic and persistent antigen, or organismal induced diseases such as Leprosy, Bacterial endocarditis, or viral hepatitis. The time cycles of each of these activated lymphocytes is specific and measurable. The T cell response is measurable at 7 days (or earlier within minutes, dependent on the detection methods used), while B cell IgM antibody production peaks at 10 days. There is thus a systematic and ultimately measurable response progression by the different cellular arms which comprise the total immune response.

One of the potential by products of any inflammatory immune response is an autoimmune reaction. Auto-immunity is a condition known to arise when T cell function and B cell-derived antibodies are initiated against self-antigens, organic self-proteins and self-peptide structures. There is an important distinction between an autoimmune reaction and an autoimmune disease, however. Autoimmune reactions, according to Matzinger, are a normal part of immune responses. They are greater early in a primary response than in a late primary or secondary response because the auto-reactive cells will eventually become tolerized by the presence of the autoantigen in the absence of second signals (Matzinger, 1994).

Autoimmune reactions are typically ephemeral. Under normal conditions, tolerance functions to delete or prevent these responses from continuing unabated. A tolerized state may be defined as the absence of specific T cell and/or B cell antibody responses to self antigens in normal individuals. It has been proposed that tolerance may occur both centrally and peripherally, and the tolerance process may involve more than one mechanism. In central tolerance, T cell precursors migrate from the bone marrow to the thymus, where variable regions on their TCR genes are assembled by somatic DNA rearrangement (Kretz-Rommel and Rubin, 2000). During this process, only maturing thymocytes with TCRs which can positively interact with self-peptides presented by the MHCs on cortical thymic epithelial cells may proceed in development (Kretz-Rommel and Rubin, 2000). T cells with a high affinity for self-peptides will be negatively selected or killed and thus impeded from proceeding as auto-reactive cells into the periphery. Their non-responsiveness to self-antigens is acquired by increasing their activation threshold to self-peptides during positive selectivity in the thymus. Recently it has been shown that certain drugs such as procaine amide and hydralazine (both known to cause Lupus) as well as non circulating localized or hidden antigen—pancreatic, thyroid, gastric—can be found in the thymus and induce tolerance by induction of Treg cells presumably by induction of Foxpro3 transcription factor.

A number of passive mechanisms have been proposed to account for peripheral tolerance including induction of T cell anergy, T cell deletion, and immunological ignorance (lack of exposure—hidden antigens—to privileged lymphoid sites). Active mechanisms that have been proposed include suppressor or regulatory T (TR) cells, including CD4+CD25+ TR cells. Important determinants in the differentiation of naïve CD4+ T cells are the APCs that stimulate them and their corresponding cytokine environment. It has been shown that IL-10 functions as a differentiating factor for TReg cells. IL-10 also prevents DC maturation, which may assist in TReg development, as T cells which are stimulated with immature DCs lead to differentiation into regulatory T cells (Maloy and Powrie, 2001). While mature DCs are potently immunogenic (Richards 2003). Recently it has shown that immature DCs can be induced to produce the FOX pro 3 gene transcription factor which has been shown to be critical in the generation of TReg cells in the thymus and the periphery. There is currently no way to delineate an exact molecular pathway for the suppression mechanism, but Maloy and Powrie have proposed a quantitative model for TReg cell induced tolerance based on the ratio of TReg cells to TPATH cells (potentially pathogenic autoreactive T cells) which respond to a peripheral antigen (Maloy and Powrie, 2001). They assert that in the lymph nodes, this ratio is dynamic and fluctuates depending on the affected/inflammatory status of local tissues. During times of homeostasis, immature DCs ("iDCs") circulate through peripheral tissues where they can phagocytose debris arising from natural cell turnover. In the absence of inflammation, some of these iDCs will migrate to the lymph nodes where presentation of self-antigens to both TReg and TPATH cells is possible. Maloy and Powrie argue that an autoimmune reaction will not be initiated because the TPATH cells are insufficiently activated by the iDCs in the absence of signal 2 and/or the iDCs preferentially stimulate TReg cells, since TReg cells can respond more efficiently to low levels of cognate peptide ligands than conventional naïve CD4+ T cells. However, the onset of an inflammatory response to a causative agent will induce DC activation and subsequent migration to the lymph nodes for presentation of antigen/pathogen protein/peptide sequences, as well as self-antigen sequences resulting from inflammatory-based tissue destruction. This DC stimulus MHC peptide (signal 1) combined with a MDI signal 2 will temporarily override TReg cell activity and functionality, since the TReg subset will also undergo cell division and clonally expand instead of actively suppressing the antigen/pathogen being presented. A very exiting new finding is that IL-6 is the single most important cytokine or MDI in overriding T reg, and in inducing specific immune reactivity (Pasare & Medzhitov 2003). As the causative agent is cleared from the system and presentation of peptides by activated DCs diminishes, any effector T cells used in the combatative response will either die or become memory cells. Without costimulation, immature DCs will again process cellular debris in a non-activated state. Since both subsets of T cells underwent proliferation, the initial ratio may be maintained, such that TReg cell regulatory activity may predominate, inhibiting TPATH cells and downregulating APCs (Maloy and Powrie, 2001). They also note that these TReg cells may migrate into the periphery and thus perform a similar function.

While the concept of an endogenous T cell suppression of immune responsiveness was first noted in the late 1960s and early 70s, a major resurgence has recently resulted in a number of critical papers by (Hori et al 2003), Koretzky 2003 Powrie 2003. In addition the use of DNA microarrays and proteomics have opened new insights into the role of Chemokines (Richards et al 2002) DCs, Cell trafficking, anatomical localization, costimulatory molecules, inhibitory and enhancing cytokines, glucocorticoid receptors, bromocriptine, and vitamin D analogues in the modulation of activation of Treg cells.

Finally, Matzinger's rules of tolerance in relation to her Danger Theory postulate that thymocytes and virgin T cells should die if they receive signal 1 in the absence of signal 2, and virgin T cells may only respond to a signal 2 offered by an APC. Effector T cells should die if they receive signal 1 in the absence of signal 2, but may receive signal 2 from a variety of different cell types. B cells should also die with receipt of signal 1 in the absence of signal 2, and should only receive this signal 2 from effector T cells. Lastly, effector cells should ignore signal 2, perform their predetermined function with the receipt of signal 1, and return to a resting state in a short time frame (Matzinger, 1994).

In all cases, the onset of auto-immune disease is considered to be the result of a disturbance in tolerance or error in some aspect of the immune response. Free radicals, reactive oxygen and nitrogen species, cytokines, oxidative reductive enzymes, prostaglandins, heat shock proteins, superantigens, and polyclonal T and B cell activators have all been suggested, but none proven (Matzinger, 1998). Examples of self-antigen links to auto-immune disease include T cell responses and B cell responses with antibodies to nucleosomes, splicing ribonucleoproteins, DNA, RNA, and Sm antigens in Systemic Lupus Erythmatosus (Casciola-Rosen et al, 1994), antibodies to alpha Topoisomerase 1 and to centromere antigens in Scleroderma (Casciola-Rosen, 1997), RNP antigens in Mixed Connective Tissue Disease (Sharp et al 1977), aminoacyl tRNA in Myositis (Tan et al 1988), antibodies to thyroid microsomal peroxidase and thyroglobulin antigens in Thyroid Disorders (Rose and McKay, 1985), and islet cell insulin and GAD65 antibodies in Diabetes Mellitus (Wucherpfennig, 2001). In these examples, it is considered that these specific T cell and antibody/B cell responses are in fact the causes of these diseases.

The two theoretical mechanisms by which infectious agents might initiate autoimmunity are currently classified as either "antigen-specific" or "antigen-nonspecific". The principle explanation for antigen-specific route to autoimmunity is epitope mimicry. The theory asserts that antigenic determinants on the proteins of a foreign microbe are similar to that of a host protein, yet different enough to recognized as foreign by the host immune system (Benoist and Mathis, 2001). An example is rheumatic fever following a Strep infection. For T cells, those determinants would be linear peptide stretches about 8-15 amino acids long. Credibility for an imperfect determinant copy has been enhanced by the fact that T cell receptor ("TCR") recognition of MHC-peptide complexes is degenerate, and doesn't require primary structure homology between two peptides presented by a given MHC molecule (Wucherpfennig, 2001; Maverakis et al, 2001). A specific immune response to the microbe could then cross-react with the overly similar host tissue, facilitating a self-antigen specific response and potential autoimmunity (Benoist and Mathis, 2001). This hypothesis is supported by the fact that pathogen-specific T cell clones cross-react with specific self-peptides and cause disease in animal models. Further support for the molecular mimicry theory comes from the fact that B cell tolerance can be broken when self-epitopes are displayed in a repetitive manner on viral surfaces (Bachmann and Kopf, 2001).

The most popular antigen-nonspecific explanation for pathogen induced autoimmunity is the bystander T cell phenomenon. Infections and other foreign pathogens result in cellular damage, either through pathogen-derived cell death or the action of cytotoxic immune cells and molecules. Self-antigens are a byproduct of necrotic cell death and may be absorbed and processed by macrophages and DCs. These APCs are then indirectly activated by non-specific factors, resulting in upregulation of costimulatory molecules and APC migration to secondary lymphoid organs where they may prime T cells to respond (Bachmann and Kopf, 2001). This supports the argument that indirect activation of APCs may trigger self-antigen lymphocyte responses and autoimmunity. It is compatible with the findings that administration of LPS together with thyroid extracts are able to overcome tolerance and trigger autoimmune thyroiditis (Weigle, 1980).

A recent finding by Ishikawa et al has shown that autoimmunity may be initiated via lymphocyte attraction to self-antigens in the periphery. Ishikawa et al induced lupus-like symptoms in transgenic mice by inducing overexpression of B lymphocyte chemokine ("BLC") in the pancreas. The physiological role of BLC is to coordinate the production and maintenance of B cell follicles in the lymph nodes and spleen by attracting CXCR5 receptor expressing B cells. Upon stimulation by BLC, B cells produce lymphotoxin B, which is essential for the generation of follicular DCs, formation of B cell follicles, and production of secondary lymphoid chemokine ("SLC"), which attracts T cells and leads to T cell regions adjacent to the B cell follicles. Ishikawa et al found that myeloid DCs rather than follicular DCs were the major producers of BLC in these afflicted organs. The study further showed that enhanced expression of BLC in DCs of these transgenic mice may attract B1 cells and T cells, creating a lymphoid environment in a non-lymphoid organ, a situation suited to cause autoimmunity (Bachmann and Kopf, 2001).

Understanding Induced Immuno-Suppression. The immune system is controlled by DCs as antigen presentation is the critical event in the induction of an Immune response. As noted above the Innate immune system has been considered to be the non specific arm of this response. Increasing evidence that commenced with understanding the nature of innate activation in *Drosophila* (the fruit fly), and the findings of: −1. The protein Spaetzle which triggers the TOLL receptor to initiate a response in the fruit fly; 2. Toll like receptors (TLRs) in man; 3. Dependence for innate activation on adapter proteins in both, and 4. The induced functional responses in both, have all now introduced a new degree of specificty to this innate system. TLR induced signal transduction comprises at least 11 TLRs. (TLR1-11) In the case of TLR2 and TLR4 the adapter protein is MyD88. Another adapter related to MyD88 has been called Mal. In addition a third addition to this family has been termed Toll-interleukin-1 receptor (TIR) domain-containing adaptor inducing interferon β (IFN-β), (TRIF), or TIR-containing adapter molecule-1 (TICAM-1) which is particularly important for activation of TLR-3 by viral antigens. Two others have also been identified in man TRAM and SARM. The importance of these new findings is, that the inducing antigens, the TLRs and the adapter proteins responding to this induction by antigens depend on both, and no longer is a single PRR or single TLR pathway sufficient to understand the mechanism of innate activation, or suppression by an antigen. (O Neill et al June 2003 Trends in Immunol).

Dendritic cells (DC) are derived from the bone marrow hemopoietic progenitor cells. The finding that DCs could be derived from peripheral blood monocytes, and from BM cells by culturing them in vitro, with appropriate growth factors, has allowed a rapidly advancing and new understanding of the mechanisms for both activation and suppression of both T and B cell responses in vitro. The function of DCs correlates with their degree of differentiation and maturation. (Richards et al Ann. Ny Acad Sci 975:91-100 2002) Immature DCs (iDCs) seem to induce Tolerance. Mature DCs are potent immune enhancers or amplifiers, at least for certain antigens such as influenza (ibid) while iDCs in the same antigen system were non immunizing but suppressing.

Attempts to profile DC responses by DNA and oligodeoxynucleotide microarrays, and proteomics have led Richards to conclude that proteomics as well as genomic studies are critical to interpret the responses to antigens by these cells in order to understand their roles in both activation and suppression. This is so because post replication transcription and translational events may alter the DNA and proteins which have been induced by antigens.

Experimental Data. The role of dsDNA as antigen in Normals and Lupus patients. In order to address this question we asked the following: a) What is the effect of mammalian dsDNA (calf thymus) origin, on inducing T cell blastogenesis of normal and lupus PBM cells? b) What is the effect of acute lupus serum on this response? c) What is the effect of this dsDNA on T cell activation of normal and Lupus cells by antigen (SK-SD), T cell mitogens PHA and Con A, and the B cell mitogen, PWM, and finally alloantigens? and d) Can dsDNA activate suppressor T cell function?

In summary, dsDNA of calf thymus mammalian origin, failed to cause T or B cell blastogenesis of either normal or Lupus patient PBMs in vitro. (is therefore non immunogenic in normals or Lupus). This is in contrast with the report of Pisetsky who used bacterial DNA as the stimulating antigen and found positive results. Oligonucleotides and CpG motifs they found yielded enhanced imunogenicity also. (Jiang and Pisetsky 2003). Mammalian dsDNA differs from bacterial DNA in the lack of CpG motifs and many of the remaining motifs are methylated and thus weakly stimulatory to B cells. (Rui et al Nature Immunol June 2003).

We next found a progressive decrease in CPMs in both normal as well as Lupus PBMs ie. (T cell suppression) when increasing doses of dsDNA-1 to 100 micrograms -were added to the cultures, and incubated with either antigens SK-SD, T cell Mitogens PHA, & ConA, and B cell mitogen PWM. This suppression was found to be dose dependent. (see Figures below).

Finally we took normal cells and incubated them for 48 hrs in vitro with either no stimulant (Control), ConA, or dsDNA by the method of Shou et al J Ex Med. 1976 v 143, 1100-1110. We found that when we added these—the 48 hr. pre-incubated cells to fresh autologous normal cells in the presence of antigens SK-SD, or the mitogens PHA, Con A, or PWM, both Con A and dsDNA 48 hr pre-incubated cells caused an equal suppression of CPMs (T & B cell division) of around 45% in the fresh PBMs when compared to the controls. Similar data was found in a one way MLC assay.

Because Con A is considered to be a measure of suppressor function in this assay, the results suggest that dsDNA normally activates or induces suppressor function of normal PBMs. Furthermore the higher the dose of dsDNA in the 48 hr pre-incubated cultures the greater the suppression. In fact complete suppression of the PWM blastogenesis (a B cell mitogen), was found when the dose of dsDNA in the preincubated cultures was 100 micrograms per culture. Thus one reason why dsDNA is non antigenic in normal and Lupus PBMs, is that it preferentially activates suppressor T cell and or monocyte function. Its loss in Lupus can thus explain the succeeding immune dysregulation which follows. Improvement with plasmapheresis and high dose corticosteroids, need now to be interpreted in this new light. (see Bresnihan et al).

These results are all in keeping with the reports starting in the late 1970s, and early 1980s which showed loss of suppressor T cell function in acute Lupus. Lupus is a heterogeneous disease where activity results from the interplay of multiple genes, multiple antibodies, and results in multiple clinical phenotypes or clinical manifestations. In order to accurately classify it clinically, one therefore has to define these variables.

Knowing that circulating immune complexes (CIC), Interferon levels, Complement levels, and dsDNA binding antibodies can all influence Monocyte, DC, and T cell function, we evaluated the effects of acute Lupus sera on the dsDNA in vitro suppression of both T and B cell blastogenesis to antigens and mitogens as we did above, in an effort to understand the role of antibodies, complement, immune complexes, and interferon levels, on T and B cell function in vitro from active and inactive Lupus patients.

We found that T cell suppression of normal T cells by dsDNA was further enhanced by the addition of acute lupus sera to the cultures. We further found that the degree of suppression was related not to Interferon, CIC, complement or DNA binding percent, levels. Rather it was related to the avidity of the IgG anti DNA antibodies. The higher the IgG avidity, the higher the T cell suppression in vitro we found. This was true for B cells also. The mechanism of this inhibition has not yet been defined. Candidates are the Fc Gamma 111R, and Complement receptor CD46 or the mannose binding or Scavenger Receptors on the monocytes in the cultures.

These results in summary identify that Mammalian CT dsDNA is not antigenic in normals or Lupus patients, and in contrast it suppresses antigen, mitogen, and alloantigen stimulation of T and B cells in vitro. That high avidity IgG anti dsDNA antibodies further increases this suppression and that one mechanism for this suppression is Activation of suppressor T cells. This dsDNA induced suppression is not antigen specific, in this system. Because dsDNA suppresses recall antigens, mitogens, and alloantigens it functions as a bystander immunosuppressant. This activation of Suppressor T cells by dsDNA is abrogated by treatment with DNAase.

All of the above ideas and findings were conceived, performed, and documented in laboratory notebook format for the first time in 1997.

These data identify a loss of suppressor T cell function in Lupus. The mechanism for this loss is not yet clear but immune over-activation by demethylated DNA caused by drugs, chemicals, inflammatory molecules, IL-6, reactive oxygen and nitrogen species, or other molecules, could lead to DC/Treg loss, due to their excessive consumption/utilization. Binding of high avidity IgG antibody, dsDNA, and complement components to immature DCs, through the CD 46 complement receptor, the Fcgamma 111R, mannose binding, scavenger, or other of the monocyte cluster of receptors, could result in cell loss from this mechanism, by apoptosis, or necrosis, or functional loss due to blockade of TLRs and their responses to immunostimulating ODNs. The association of leucopenia with acute flares, and the finding of antilymphocyte antibodies, with and without T cell suppressing activity, are in support of this thinking. It is of interest also that high corticosteroid dose which is normally considered to be immunosuppressive, in Lupus paradoxically is immune-enhancing. Bresnihan showed a return of suppressor T cell function following their use. Low complement levels rise, CICs fall and Treg function returns to normal, coterminous with clinical improvement, following upon their use. (It is now known that the GITR receptor on T regs, is steroid activated and important in their activation).

The precise mechanism whereby CT dsDNA induces T cell dependent T and B cell suppression is not yet clear. All of the data reviewed suggests that both DCs, and T cell contact dependence, as well as soluble factor(s) are involved. Thymic factors—thymosine, thymopoietin, TsIF, SIRS, and the cytokines IL-10, and TGFβ have all been suggested. The TLRs involved, the signaling pathways downstream of cell membrane activation, the induction of the Foxpro3 gene are all intriguing findings for future pursuit. Recent findings of the innate TLRs being found on the CD 4 cells themselves pose questions as to whether these molecules can be both immune enhancing and suppressing.

The availability of a natural vaccine product which will induce immune suppression, which is not antigen specific, which affords time and dose flexibility, and immune parameter monitoring, is a major advantage to our current armamentarium, in diseases such as Lupus, Rheumatoid Arthritis, Scleroderma, Polymyositis, Mixed Connective Tissue Disease, and vasculitis, where steroids and chemotherapeutic agents with their inherent major toxicities, are the current standard of care. Attempts to use anti TNFs in Lupus and Sjogrens have not been successful to date, and even deleterious. Successful use of the embodiment in GvH and HvG disease could have a dramatic impact on the treatment of kidney, liver, heart, and isolated organ failures, and their treatment by organ grafting; and in Bone Marrow and/or stem cell grafts now used for the treatment of refractory Connective Tissue diseases, Cancer, and bone marrow failure. A positive impact on Alzheimers Disease, Coronary Artery disease and stroke, and systemic Amyloidosis, diseases where no current strategies to alter chronic inflammation are available, would have a revolutionary impact on high morbidity, high mortality, high cost diseases, which currently contribute in a major way to the health care expenditure in the US of 12% of the annual GDP. Finally the potential for its use early in HIV AIDS where loss of Tregs has now been reported at the time of reduction of T cell numbers and function which is the hallmark of this illness. Those with strong or vigorous T regulator function were found to have lower levels of viremia and higher CD 4 and CD 8 cell counts. (Kinter et al J Ex Med 2004 Aug. 2; 200(3):331-334).

Calf Thymus DNA. Calf Thymus is obtained from the abbatoir, and the DNA is prepared by the method of Marmur J. Mol Biol 5.109 1962, by homogenizing it in a blender. It is then purified by equilibrium buoyant density gradient ultracentrifugation in cesium chloride, dialyzed against a solutuion of 1 mM sodium chloride, 1 mM EDTA and 1 mM Trizma HCL, pH 7.5, and lyophilized at a concentration of approximately 2 units per ml. Approximately 20 A260 units equal 1 mg DNA. The DNA quality and integrity are evaluated using pulsed field gel electrophoresis after ethidium bromide staining. The DNA is free of RNA and endotoxin, contaminants that might interfere with endonuclease digestion. No nuclease activity was detected after 16 hr at 37° incubation. The product is sterilized by gamma irradiation, and lyophilized in vials at 100 mg each. It is solubilized in 0.95% physiological saline for intramuscular or subcutaneous administration.

Synthetic DNA. Synthesis of DNA, in vitro, is routine in the art. As is known to persons of skill in the art, synthetic DNA may be prepared using automated devices. Alternatively, persons of skill in the art may prepare synthetic DNA by PCR and similar enzymatic methods.

Methylation of DNA. Two DNA methylation activities are required in mammalian nuclei. A first type, maintenance methylation, is responsible for adding methyl groups to the appropriate positions on newly synthesized DNA polynucleotides ensuring that the methylation pattern of the parent DNA is maintained by the daughter double helices after genome replication. The second type of activity is de novo methylation, which changes the methylation pattern of a DNA molecule by adding new methyl groups in a tissue-specific manner, resulting in programmed changes in genome expression patterns. The DNA methyltransferase 1 enzyme (Dnmt1) is responsible for maintenance methylation and displays de novo methylation activity in vitro. De novo methylation is primarily catalyzed by the Dnmt3a and Dnmt3b enzymes. Persons of skill in the art are familiar with techniques for enzymatic methylation of DNA, in vitro (Lu S. and Davies J A, 94 P.N.A.S. 4692 (1996)).

Pharmaceutical compositions. Pharmaceutical compositions are taught generally by Remington's Pharmaceutical Sciences (Gennaro et al., eds., Remington: The Science and Practice of Pharmacy, 20$^{th}$ Ed., Lippincott Williams & Wilkins, Baltimore, Md. (2000)) the disclosure of which is hereby incorporated by reference.

Vaccination. The IM route is preferred in order for the preparation to come in contact with interstitial DCs. Subsequent migration to the lymph nodes is anticipated. The MW of the whole dsDNA will be cut by a French press to yield an average size in MW between 10 and 50 k Daltons.

Vaccination means delivery of the embodiment by any appropriate route, including, but not limited to, intradermal, subcutaneous, and intramuscular injection(s), as well as by oral and nasal inhalation as is known by those skilled in the art. Vaccines and vaccination techniques are disclosed generally in Remington's Pharmaceutical Sciences (Gennaro et al., eds., Remington: The Science and Practice of Pharmacy, 20$^{th}$ Ed., Lippincott Williams & Wilkins, Baltimore, Md. (2000)) the disclosure of which is hereby incorporated by reference.

Sequence Determination of CTDNA. The published sequence analysis of bovine I DNA (Nucleic Acids Res Taparowsky EJ et al 1982) was 97% homologous to the sequence reported for another clone of satellite I and for another uncloned satellite I DNA. The most outstanding repeat structures center on the hexanucleotide 'ctcgag' (SEQ ID NO: 3) which occurs at 26 locations within the EcoRI repeat. Two of these 6 bp units are found within the 31 bp consensus sequence of a repeating structure which spans the entire length of the 1402 bp repeat. The clustering of methylated cytosines (mc) in CT DNA (Proc Natl Acad Sci 1982 Sano H and Sager R p3584-3588) was found to be non random and clustered at positions 300-500, 800-1000, and 1200-1400. All mcs were located in cg doublets, and better than half were in short palindromes 'ccgg' (SEQ ID NO: 4) and 'tcga' (SEQ ID NO: 5) and appear 10 to 16 times respectively. Thus the frequency of CpGs is less and the degree or frequency of methylation is greater than in human DNA. This frequency distribution of CpG islands in human chromosomes 21 and 21 have been reported and compared with D Melanogaster and S cerevisiae (PNAS March 2002, 3740-3745. Takai et al) they found 5,039 CpG islands on chromosome 21 and 9,023 on chromosome 22 or 50 fold more than anticipated. Lennert et al in an abstract #11 presented at ARA October 2003 reviewed the data on stimulatory, neutral, and inhibitory oligodeoxynucleotides (ODNs). They found stimulatory ODNs activated B cells, DCs and macrophages, which was inhibited by inhibitory ODNs (IN ODNs), and that this was specific as the latter did not inhibit LPS or mitogens such as anti CD 40. They thus felt that IN ODNs competed for the Receptor now known to be TLR 9. They found also that single base pair changes with profound effects on IN ODNs potency were clustered at 3 pairs of positions in the 15-mer sequence which they called Hot Spots. Telomeric hexamers with the sequence TTAGGG (SEQ ID NO: 2) they found to be inhibitory. They concluded that DNA sequences can be both stimulatory and inhibitory, and that the potency for both is dependent on the affinity of the 5' end of ODNs for a recognition molecule whereas the 3' end or Hotspots determine whether the ODN is stimulatory or inhibitory. Gursel et al J Immunol. 171:1393-1400 2003 confirmed these findings and that repetitive elements were present with high frequency in mammalian telomeres, rare in bacteria, & were inhibitory to CpG stimulation. The suppressive activity correlated with the ability of the telomeric TTAGGG (SEQ ID NO: 2) repeats to form G-tetrads. Colocalization of both on TLR9 endosomal vesicles was the cause of this suppression.

The inference from these findings is that self or mammalian DNA has the ability to down regulate bacterial stimulation of B cells DCs and macrophages, and therefore protect from over exuberant "Inflammation" caused by bacterial species. Stacey et al (J of Immunol 170: 3614-3620 2003) examined vertebrate DNA for its lack of stimulatory capability. They found general CpG suppression, CpG methylation, inhibitory motifs, and saturable DNA uptake combined to explain the inactivity of self DNA They also found that G-rich sequences such as GGAGGGG (SEQ ID NO 1) were potent inhibitors of stimulation. None of these papers addressed a role for Tregs as a mechanism for this suppression. It is of interest that Telomere erosion has been associated with aging, immune deficiency, cell senescence, persistent immune activation, autoimmunity, Alzheimers Disease, Systemic Lupus, and Rheumatoid Arthritis. The mechanisms have been attributed to persistent cellular activation, reactive oxygen and nitrogen species, free radical accumulation and others. All of these illnesses have been already associated with Suppressor/Regulator T cell deficiency. These new findings would appear to support a possible linkage between Telomeric Erosion, Treg loss, immune dysregulation and disease. They support also a need for a method for induction and maintenance of suppressor T cell function, which this embodiment provides. Based upon these findings the embodiment will be checked to ensure the presence of both the G rich sequences GGAGGGG (SEQ ID NO: 1), and the telomeric sequences TTAGGG (SEQ ID NO 2) in the tetrad format before use.

A Role for the Gut in Immunosuppresion. The frequency of autoimmune disease Asthma, Crohns, Ulcerative colitis, Diabetes, Multiple Sclerosis have all been shown to have increased dramatically in developed Western societies. Lupus as one example has a far higher prevalence in the USA when compared with a genetically similar African domiciled population of blacks. This has been ascribed to what is now called the Hygiene Hypothesis which implies that a clean environment may be "Dangerous" for ones health, in that not enough Danger signals (see Matzinger) are being generated in the over protected societies—Use of antibiotics, vaccinations, sterilizing agents in the homes—prevent children from organismal exposures in the food, water, air, etc. Studies in Europe have supported this in that children in a rural farm environment had a reduced prevalence of Asthma and allergies compared to their city brethren. The explanation was a higher exposure rate to bacterial species on the farms. This was supported by the findings of Endotoxin in the bedding of those protected, by what was ascribed to Innate Endotoxin Tolerance. Similar findings in support of this thinking have come from Brazil where it was found that children who suffered from endemic worms had a low frequency of asthma, and after treatments with vermiculo-cides the incidence of asthma increased. Other studies on dextran induced colitis in animals found that feeding DNA with unmethylated CpGs could abrogate the colitis. These new studies have provided a major paradigm shift in our understanding of the role of immune homeostasis in both preventing and controlling autoimmune disease. They have reintroduced a new understanding of the role of the gut as a unique immune organ in the induction of immune homeostasis, and its regulation. Thus probiotics commensal organisms and worms or eggs from them, have now been shown to lessen, abrogate, or suppress Autoimmunity. (See Science Jul. 9, 2004 on Immunotherapy, and page 171 "Wielding Worms at Asthma and Autoimmunity" for a review of this topic). The mechanisms whereby these environmental manipulations which appear to control both the TH 1 and TH 2 diseases listed are now being ascribed to suppressor/regulator T cell induction, are in support of both the concept and methods of delivery for the embodiment.

Use in Lupus. Lupus patients for study will fulfill at least 4 of the revised ACR criteria for this diagnosis. Initially patients with a history of nephritis without permanent renal damage, as manifested by the presence of proteinuria, celluria, and or red cell or white cell casts, but with normal renal function, measured by BUN and Creatinine, and creatinine clearance levels will be selected. The rationale for this choice is that Nephritis is associated with the worst outcomes in morbidity and mortality from this disease. Immunological parameters will also be measured at the outset and serially as follows. ANA, dsDNA, C3, C4, Ch50, IgG, IgA, IgM, WCC, ESR, Cardiac CRP, and IL-6, IL-1, IL-10, TGFβ and TNFα levels will be obtained. PBMs will be collected from peripheral blood and CD4, CD8, CD4/CD8 ratios, & CD4+ CD25+ cell numbers will be identified by FACS. Functional assays on PBMs in tissue culture in response to recall antigens SK/SD, PPD, and the T cell and B cell mitogens PHA Con A and PWM and will be measured as CPMs by tritiated thymidine incorporation into DNA by scintillation counting. Vaccination will commence weekly, the dose and duration of which will depend on the clinical and immunological responses, which will be measured monthly. Subsequent use will be in early Lupus before the onset of flares of the disease.

Use in Rheumatoid Arthritis (RA). RA patients will be chosen based upon fulfilling the ARA criteria for this diagnosis. The laboratory parameters to be measured will be the same as for Lupus with the addition of Rheumatoid Factor levels. Additionally baseline X Rays will be obtained of the hands, feet, and Cervical spine.

Use in Mixed Connective Tissue Disease (MCTD), Scleroderma (PSS) and Polymyositis (PM). MCTD PSS and PM patients will be chosen upon fulfilling the ARA criteria for these diagnoses. The laboratory parameters to be measured will be the same as for Lupus with the addition of the following additional tests—CPK and Aldolase enzymes, Sm RNP and Jo1 antibodies. Vaccination will commence weekly, the dose and duration of which will depend on the clinical and immunological results, and the immune parameters will be measured monthly.

Use in Coronary Artery Disease (CAD). CAD patients will be chosen based upon the presence of new onset angina, evidence of narrowing of any of the coronary arteries on angiography, or the history of a prior heart attack. Vaccination will commence as soon as subjects consent after full information disclosure. Laboratory parameters will be measured as follows: Cholesterol levels with full lipid profile, ESR Westergren, Cardiac CRP, Homocsyteine, IL-6, IL-10, TGFβ, and TNFα levels will all be assayed at the outset and monthly after commencement of vaccination. Clinical outcomes will measure the events of hospitalization, cardiac symptoms of progressive angina, or heart attack as defined by the treating cardiologist. Statistical analysis of the results will compare a non treated control group with the treated group.

Use in Amyloidosis. As soon as the diagnosis of this disease is made by rectal, gum, fat, or organ biopsy and the biopsy results after congo red staining confirm the diagnosis, vaccination will commence. An untreated control group will be necessary. The only significant outcome for this disease is length of survival, as untreated the outcome is poor. Quantity of amyloid, organ dysfunction and the like are not meaningful parameters to measure at this time. The immune parameters as identified for Lupus will however be measured in the hope that they will be altered by the vaccination and be indicators of improvement.

Use in Alzheimers Disease (AD). Alzheimers disease will be diagnosed by the treating Neurologist and be based upon MMPI and a brain imaging study MRI CT or SPECT scans, showing brain atrophy at the frontal temporal locations typical for AD: All the immune parameters as set out for Lupus will be measured at the outset and be measured serially. Vaccination will commence weekly for 4 weeks, and then will be given at weekly, biweekly, or monthly intervals to maintain normal regulator T cell levels and normal T cell function.

Use in Vasculitis. Vasculitis will be diagnosed based upon the clinical findings and positive biopsy results. The diagnosis of Vasculitis includes both large and small vessel vasculitis, Wegeners Granulomatosis, Churg and Strauss Vasculitis, Temporal Arteritis, drug induced vasculitis, with infectious causes being excluded, including bacterial, viral including Hepatitis A, B, and C, EBV, CMV, and herpes viruses. Immune parameters as in the Lupus study will be performed at the outset and serially with the inclusion of anti neutrophil cytoplasmic antibodies ANCA, both P and C type. Vaccination will commence weekly for 4 weeks, and then at weekly, biweekly, or monthly intervals, dependent on the clinical and immunological responses.

Use in HvG disease. The host response to allogeneic grafting of individual organs results in diseases termed HvG disease, characterized by systemic inflammation affecting the skin the bowel caused by the host T cells and DCs attacking the "foreign cells in the graft". The result is a systemic illness culminating in rejection and failure of the grafted organ. The embodiment will be given to the host weekly for 4 weeks prior to grafting and serially thereafter, based upon measuring the immune parameters as outlined for Lupus. It is expected that both the T and DC function will be suppressed, thereby abrogating the host rejection process and allowing successful grafting.

Use in GvH disease. The donor cells being foreign, and pluripotent as they are found in bone marrow and stem cells, contain all of the immune cell functional components for both survival in a hostile environment and for rejection of cancer. When seeing foreign cells in the recipient or host they commence the rejection process-GvH disease. This may be lethal unless controlled by immuno-suppressants. Fortunately newer agents are now available which are successful in blunting and blocking the induced responses, they are all potentially toxic however. The availability of a biologic vaccine to effect T and DC suppression of the donor cells prior to the grafting procedure offers a new potentially non toxic method to allow bone marrow and stem cell transplantation and the avoidance of GvH diseases in the recipients or hosts. The embodiment will be given to the donor by weekly injections for 4 weeks prior to donor cell harvesting. CD 4+ CD 25+ Cell numbers and function will be measured prior to and weekly following vaccinations.

SEQUENCE LISTING

A paper copy of a SEQUENCE LISTING is appended following page 66. A computer readable copy of the SEQUENCE LISTING is submitted on an accompanying CD-ROM. The contents of the paper copy and the computer readable copy are the same. The SEQUENCE LISTING merely sets forth sequences as present in the original disclosure and do not include new matter. The entire contents of the SEQUENCE LISTING, is specifically incorporated by reference.

INCORPORATION BY REFERENCE

Throughout this application, various references including publications, patents, and pre-grant patent application publications are referred to. Disclosures of these publications in their entireties are hereby incorporated by reference into this application to more fully describe the state of the art to which this invention pertains. It is specifically not admitted that any such reference constitutes prior art against the present application or against any claims thereof. All publications, patents, and pre-grant patent application publications cited in this specification are herein incorporated by reference, and for any and all purposes, as if each individual publication or patent application were specifically and individually indicated to be incorporated by reference. In the case of inconsistencies the present disclosure will prevail. Specifically, co-pending application Ser. No. 11/244,141, is hereby incorporated by reference for all purposes.

Abbas, Abul, Lichtman, Andrew, Pober, Jordan. Cellular and Molecular Immunology. 1994. W B Saunders Company Publ.

Abbas, A. K., K. M. Murphy & A. Sher. 1996. Functional diversity of helper T lymphocytes. Nature 383: 787.

Aderem A, Ulevitch R J. Toll-like receptors in the induction of the innate immune response Nature. 406.782-787 2000.

Andrade F, Casciola-Rosen L, Rosen A. Apoptosis in systemic lupus erythematosus. Clinical implications. Rheum Dis Clin North Am. 2000 May; 26 (2):215-27.

Abdou, N. I., H. B. Lindsley, et al. (1981). "Plasmapheresis in active systemic lupus erythematosus: effects on clinical, serum, and cellular abnormalities. Case report." Clin Immunol Immunopathol 19(1): 44-54.

Abe, T., C. Morimoto, et al. (1983). "Functional differences of anti-T-cell antibody in patients with systemic lupus erythematosus and ulcerative colitis." Scand J Immunol 18(6): 521-30.

Adamian, N. V., S. K. Solov'ev, et al. (1989). "[Disturbance of immunogenesis in patients with systemic lupus erythematosus]." Ter Arkh 61(5): 43-5.

Akashi, Y., S. Oshima, et al. (1995). "[Identification and analysis of immune cells infiltrating into the glomerulus and interstitium in lupus nephritis]." Nihon Rinsho Meneki Gakkai Kaishi 18(5): 545-51.

Alarcon-Segovia, D. and A. Ruiz-Arguelles (1978). "Decreased circulating thymus-derived cells with receptors for the Fc portion of immunoglobulin G in systemic lupus erythematosus." J Clin Invest 62(6): 1390-4.

Alarcon-Segovia, D. and R. Palacios (1981). "Human post-thymic precursor cells in health and disease. IV. Abnormalities in immunoregulatory T cell circuits in mixed connective tissue disease." Arthritis Rheum 24(12): 1486-94.

Alarcon-Segovia, D. and R. Palacios (1981). "Differences in immunoregulatory T cell circuits between diphenylhydantoin-related and spontaneously occurring systemic lupus erythematosus." Arthritis Rheum 24(8): 1086-92.

Alarcon-Segovia, D. (1982). "Cellular immunity and its regulation in SLE." Clin Rheum Dis 8(1): 63-75.

Alarcon-Segovia, D. (1983). "Mixed connective tissue disease: a disorder of immune regulation." Semin Arthritis Rheum 13(1 Suppl 1): 114-20.

Alarcon-Segovia, D. (1982). "Cellular immunity and its regulation in SLE." Clin Rheum Dis 8(1): 63-75.

Abdou, N. I., A. Sagawa, et al. (1976). "Suppressor T-cell abnormality in idiopathic systemic lupus erythematosus." Clin Immunol Immunopathol 6(2)92-9.

Abdou, N. I., H. B. Lindsley, et al. (1981). "Plasmapheresis in active systemic lupus erythematosus: effects on clinical, serum, and cellular abnormalities. Case report." Clin Immunol Immunopathol 19(1): 44-54.

Aldo-Benson, M. (1989). "Investigations of intrinsic abnormalities in DNA-specific B lymphocytes from autoimmune mice." J Autoimmun 2(3): 269-82.

Akbari, O., R. H. DeKruyff & D. T. Umetsu. 2001. Pulmonary dendritic cells producing IL-10 mediate tolerance induced by respiratory exposure to antigen. Nat. Immunol. 2: 725-731.

Arimori, S., K. Koriyama, et al. (1980). "T lymphoreceptopathy in systemic lupus erythematosus." Tokai J Exp Clin Med 5(4): 385-98.

Arend William P. The Innate Immune System in Rheumatoid Arthritis. Arthritis and Rheumatism 2001; Vol 44 No. 10 2224-2234.

Arnett F C, Harrington S M, Bloch D A, at al. The American Rheumatism Association 1987 revised criteria for classification of rheumatoid arthritis. Arthritis & Rheum 1988; 31: 315-324.

Bach J F The Effect of Infections on Susceptibility to Autoimmune and Allergic Diseases. NE J Med v 347; 911-920 2002

Bacchetta, R., M. Bigler, J.-L. Touraine, et al. 1994. High levels of interleukin 10 production in vivo are associated with tolerance in SCID patients transplanted with HLA mismatched hematopoietic stem cells. J. Exp. Med. 179: 493-502.

Bach, J. F. (1984). "The immunological basis of inflammatory diseases." Inflammation 8 Suppl: S43-8.

Bach, M. A. and J. F. Bach (1981). "Imbalance in T cell subsets in human diseases." Int J Immunopharmacol 3(3): 269-73.

Balestrieri, G., A. Tincani, et al. (1982). "[Evaluation of T suppressor activity in systemic lupus erythematosus]." Boll Ist Sieroter Milan 61(4): 330-5.

Ballieux, R. E. and C. J. Heijnen (1983). "Immunoregulatory T cell subpopulations in man: dissection by monoclonal antibodies and Fc-receptors." Immunol Rev 74: 5-28.

Ballow, M. and A. Parke (1989). "The uses of intravenous immune globulin in collagen vascular disorders." J Allergy Clin Immunol 84(4 Pt 2): 608-12.

Basu, S., R. J. Binder, R. Suto, et al. 2001. Necrotic but not apoptotic cell death releases heat shock proteins, which deliver a partial maturation signal to dendritic cells and activate the NF-κB pathway. Intl. Immunol. 12: 1539-1546.

Bauer, S., C. J. Kirschning, H. Hacker, et al. 2001. Human TLR9 confers responsiveness to bacterial DNA via species-specific CpG motif recognition. Proc. Natl. Acad. Sci. USA 98: 9237-9242.

Bensinger, S. J., A. Bandeira, M. S. Jordan, et al. 2001. Major histocompatibility complex class II-positive cortical epithelium mediates the selection of CD4+25+ immunoregulatory T cells. J. Exp. Med. 194: 427-438.

Blanco, P., A. K. Palucka, M. Gill, et al. 2001. Induction of dendritic cell differentiation by IFN-$_\alpha$ in systemic lupus erythematosus. Science 294: 1540-1543.

Blander J M and Medzhitov R Regulation of Phagosome Maturation by Signals from Toll-Like Receptors Science 2004 304: 1014-1018.

Bi, L. Q., Y. Song, et al. (1990). "[Lymphocyte phenotypes and their correlation with clinical features in systemic lupus erythematosus (SLE)]." Zhonghua Nei Ke Za Zhi 29(12): 720-2, 764-5.

Blank, M., M. Ben-Bassat, et al. (1991). "Modulation of SLE induction in naive mice by specific T cells with suppressor activity to pathogenic anti-DNA idiotype." Cell Immunol 137(2): 474-86.

Blank, M., I. Krause, et al. (1995). "Bromocriptine immunomodulation of experimental SLE and primary antiphospholipid syndrome via induction of nonspecific T suppressor cells." Cell Immunol 162(1): 114-22.

Bonomini, V., A. Vangelista, et al. (1984). "Effect of plasmapheresis on cellular immunity abnormalities in patients with systemic lupus erythematosus." Clin Nephrol 22(3): 121-6.

Bouzahzah, F., et al. 2003. CD4+ T cells from lupus-prone mice avoid antigen specific tolerance induction in vivo. J. Immunol. 170: 741-748.

Borel, Y. and M. C. Young (1980). "Nucleic acid-specific suppressor T cells." Proc Natl Acad Sci USA 77(3): 1593-6.

Bresnihan, B. and H. E. Jasin (1977). "Suppressor function of peripheral blood mononuclear cells in normal individuals and in patients with systemic lupus erythematosus." J Clin Invest 59(1): 106-16.

Bretscher P. Cohn M. The two-signal hypothesis: A theory of self-non slef discrimination: paralysis and induction involve the recognition of one and two determinants on an antigen, respectively. 1970. Science 169.1042-1049.

Bretscher P, Cohn M. A theory of self non self discrimination. 1970. Science 169:1042-1049.

Billingham R E, Brent L, & Medawar P B. Demonstration of specific acquired tolerance: Actively acquired tolerance of foreign cells. 1953. Nature 172; 603-606.

Breitner J C, Zandi P P. Do Nonsteroidal Anti-inflammatory Drugs Reduce the Risk of Alzheimers Disease.? New Eng J Med 345.21 1567-1568 2001.

Breitner J C. Inflammatory processes and ant-inflammatory drugs in Alzheimers Disease: a current appraisal. Neurobiol. Aging 17 789-794 1996.

Burnet F M. The Clonal Selection Theory of Antibody Formation. 1959 Publisher Cambridge University Press London.

Bellanti Joseph. Immunology. 1971 WB Saunders Co, London Bachmann, Martin and Kopf, Manfred. On the role of the innate immunity in autoimmune disease. J Exp Med. 2001 193 (12): 47-50.

Benoist, Christophe and Mathis, Diane. Autoimmunity provoked by infection: how good is the case for T cell epitope mimicry? Nature Immunology 2001 2, 797-801.

Bickerstaff, M C M et al. Serum amyloid P component controls chromatin degradation and prevents antinuclear autoimmunity. Nature Medicine. 1999 Vol 5, No 6. 694-697.

Bunn C C, Bernstein R M, Mathews M B. Autoantibodies against alanyl-tRNA synthetase and tRNA Ala coexist and are associated with myositis. 1986. J Exp Med 163: 1281-1291.

Caciola-Rosen L A, Anhalt G, Rosen A. Autoantigens targeted in systemic lupus erythematosus are clustered in the two populations of surface structures on apoptotic keratinocytes. J. Exp. Med 1994 Apr. 1; 179(4):1083.

Casciola-Rosen L, Wigley F, Rosen A. Scleroderma autoantigens are uniquely fragmented by metal catalyzed oxidation reactions: implications for pathogenesis. J. Exp. Med 1997 Jan. 6; 185(1):71-9.

Castronova V et al Silicosis and Coal Workers Pneumoconiosis Environ Health Persp. V108 suppl4 p 675-684.

Calabrese, L. H., J. F. Bach, et al. (1981). "Development of systemic lupus erythematosus after thymectomy for myasthenia gravis. Studies of suppressor cell function." Arch Intern Med 141(2): 253-5.

Casciola-Rosen L, Andrade F, Ulanet D, Wong W B, Rosen A. Cleavage by granzyme B is strongly predictive of autoantigen status: implications for the initiation of autoimmunity. J. Exp. Med 1999 Sep. 20; 190(6):815-26.

Chee, Y. C. (1982). "Cellular immunological dysfunction in systemic lupus erythematosus." Singapore Med J 23(1): 12-8.

Chen, Y., P. Lenert, R. Weeratna, et al. 2001. Identification of methylated CpG motifs as inhibitors of the immune stimulatory CpG motifs. Gene Ther. 8: 1024-1032.

Chiller J M, Habicht G, Weigle W O. Cellular sites of immunological unresponsiveness. 1970. Proc. Natl. Acad. Sci. USA 65; 551-556.

Cocco R E, Ucker D S. Distinct Modes of Macrophage Recognition for Apoptotic and Necrotic Cells are Not Specified Exclusively by Phosphatidylserine Exposure. Mol. Biol Cell April 2001; 12 (4):929-930.

Coleman C W Homeostatic Processes in Brain Aging; The role of Apoptosis, Inflammation, and Oxidative Stress in Regulating Healthy Neural Circuitry in the Aging Brain in The Aging Mind: Appendix B 2000. Nat'l Academy Press p 114.

Cowdery, J. S., J. H. Chace, A.-K. Yi & A. M. Krieg. 1996. Bacterial DNA induces NK cells to produce IFN gamma in vivo and increases the toxicity of lipopolysaccharides. J. Immunol. 156: 4570-4575.

Cheong, S. K., S. F. Chin, et al. (1997). "Lymphocyte subsets in systemic lupus erythematosus." Malays J Pathol 19(2): 121-5.

Cledes, J., J. P. Herve, et al. (1983). "[Pulmonary silicosis and disseminated lupus erythematosus]." Poumon Coeur 39(4): 205-7.

Clough, J. D., S. A. Frank, et al. (1980). "Deficiency of T cell mediated regulation of anti-DNA production in systemic lupus erythematosus." Arthritis Rheum 23(1):24-9.

Clough, J. D., R. A. Krakauer, et al. (1980). "Allogeneic suppression of polyclonal immunoglobulin production in normals and patients with systemic lupus erythematosus." Clin Exp Immunol 42(1): 27-32.

Coovadia, H. M., I. R. MacKay, et al. (1981). "Suppressor cells assayed by three different methods in patients with chronic active hepatitis and systemic lupus erythematosus." Clin Immunol Immunopathol 18(2): 268-75.

Corrigall V, O'Neill A J Using Immunotherapy to treat rheumatic diseases Trends in Immunol vol 23 no 8 p 384 2002.

D'Cruz D, Autoimmune diseases associated with drugs, chemicals and environmental factors. Toxicol Lett 2000 Mar. 15; 112-113:421-432.

Cooper G S, Miller F S, Pandey J P. The role of genetic factors in autoimmune disease: implications for environmental research. Environ Health Perspect 1999 October; 107 Suppl 5:693-700.

Croston, G. C., Z. Cao & D. V. Goeddel. 1995. NF-κB activation by IL-1 requires an IL-1 receptor associated protein kinase activity. J. Biol. Chem. 270: 16514-16517.

Czernicki, J., M. Offierska, et al. (1981). "[Suppressor cell activity in multiple sclerosis and other nervous system diseases. Preliminary report]." Neurol Neurochir Pol 15(3): 283-9.

Dau, P. C., J. Callahan, et al. (1991). "Immunologic effects of plasmapheresis synchronized with pulse cyclophosphamide in systemic lupus erythematosus." J Rheumatol 18(2): 270-6.

Deng, G. M. & A. Tarkowski. 2000. The features of arthritis induced by CpG motifs in. Arthritis Rheum. 43: 356-364.

Deng, G. M., I. M. Nilsson, M. Verdrengh, et al. 1999. Intra-articularly localized bacterial DNA containing CpG motifs induces arthritis. Nat. Med. 5: 702-705.

Dieckmann, D., H. Plottner, S. Berchtold, et al. 2001. Ex vivo isolation and characterization of CD4(+) CD25(+) T cells with regulatory properties from human blood. J. Exp. Med. 193: 1303-1310.

Drannik, G. N., G. I. Lysenko, et al. (1980). "[Functional activity of nonspecific T-lymphocyte suppressors in health persons and in systemic lupus erythematosus patients]." Vrach Delo (1): 88-90.

Dhodapkar, M. V. & R. M. Steinman. 2002. Antigen-bearing, immature dendritic cells induce peptide-specific, CD8+ regulatory T cells in vivo in humans. Blood 100: 174-177.

Dhodapkar, M. V., J. Krasovsky, R. M. Steinman, et al. 2000. Mature dendritic cells boost functionally superior T cells in humans without foreign helper epitopes. J. Clin. Invest. 105: R9-R1.

Dhodapkar, M. V., R. M. Steinman, J. Krasovsky, et al. 2001. Antigen specific inhibition of effector T cell function in humans after injection of immature dendritic cells. J. Exp. Med. 193: 233-238.

Driessen, C., Lennon-Dumenil, A. M. & Ploegh, H. L. Individual cathepsins degrade immune complexes internalized by antigen-presenting cells via Fcγ receptors. Eur. J. Immunol. 31, 1592-1601 (2001).

Elkins, K. L., T. R. Rhinehart-Jones, S. Stibitz, et al. 1999. Bacterial DNA containing CpG motifs stimulates lymphocyte-dependent protection of mice against lethal infection with intracellular bacteria. J. Immunol. 162: 2291-2298.

Engering, A., T. B. Geijtenbeek, S. J. van Vliet, et al. 2002. The dendritic cell-specific adhesion receptor DC-SIGN internalizes antigen for presentation to T cells. J. Immunol. 168: 2118-2126.

Fadok, V. A., D. L. Bratton, A. Konowal, et al. 1998. Macrophages that have ingested apoptotic cells in vitro inhibit proinflammatory cytokine production through autocrine/paracrine mechanisms involving TGF-beta, PGE2, and PAF. J. Clin. Invest. 101: 890-898.

Fearon, D. T. & R. M. Locksley. 1996. The instructive role of innate immunity in the acquired immune response. Science 272: 50-54.

Filaci, G., S. Bacilieri, et al. (2001). "Impairment of CD8+ T suppressor cell function in patients with active systemic lupus erythematosus." J Immunol 166(10): 6452-7.

Gattringer, C. and H. Huber (1983). "[Immunologic detection and in vitro activity of suppressor cells]." Wien Klin Wochenschr 95(5): 138-44.

Gattringer, C., H. Huber, et al. (1982). "Normal suppressor-cell activity in systemic lupus erythematosus. A study on 26 cases." Immunobiology 163(1): 48-52.

Gershon R K, A disquisition on suppressor T cells. Transplant Rev. 1995; 26, 170-185.

Gladman, D., E. Keystone, et al. (1980). "Impaired antigen-specific suppressor cell activity in patients with systemic lupus erythematosus." Clin Exp Immunol 40(1): 77-82.

Gleichmann, E. and H. Gleichmann (1985). "Pathogenesis of graft-versus-host reactions (GVHR) and GVH-like diseases." J Invest Dermatol 85(1 Suppl): 115s-120s.

Gordovskaia, N. B., V. N. Denisov, et al. (1982). "[T-suppressor functional activity in systemic lupus erythematosus and chronic glomerulonephritis]." Ter Arkh 54(7): 29-32.

Gottlieb, A. B., R. G. Lahita, et al. (1979). "Immune function in systemic lupus erythematosus. Impairment of in vitro T-cell proliferation and in vivo antibody response to exogenous antigen." J Clin Invest 63(5): 885-92.

Green, B. J., D. G. Wyse, et al. (1988). "Procainamide in vivo modulates suppressor T lymphocyte activity." Clin Invest Med 11(6): 425-9.

Gregorini G et al. Association between silica exposure and necrotizing crescentic glomerulonephritis with p-ANCA ans anti-MPO antibodies: a hospital based case control study. Adv Exp Med Biol 440:336-435 1993.

Griem P, Wulferink M, Sachs B, Gonzalez J B, Gleichmann E. Allergic and autoimmune reactions to xenobiotics: how do they arise? Immunol Today 1998 Mar. 19 .3. 133-141.

Gupta, S. (1983). "Autologous mixed lymphocyte reaction in health and disease states in man." Vox Sang 44(5): 265-88.

Gursel, M., D. Verthelyi, I. Gursel, et al. 2002. Differential and competitive activation of human immune cells by distinct classes of CpG oligodeoxynucleotides. J. Leukocyte Biol. 71: 813-819.

Gursel I. et al., 2003. Repetitive elements in mammalian telomeres suppress bacterial DNA-induced immune activation. J Immunol. 171(3):1393-400.

Habersetzer, R., W. Samtleben, et al. (1983). "Plasma exchange in systemic lupus erythematosus." Int J Artif Organs 6 Suppl 1: 39-41.

Hacker, H., H. Mischak, T. Miethke, et al. 1998. CpG-DNA-specific activation of antigen-presenting cells requires stress kinase activity and is preceded by non-specific endocytosis and endosomal maturation. EMBO J. 17: 6230-6540.

Halpern, M. D. & D. S. Pisetsky. 1995. In vitro inhibition of murine IFN gamma production by phosphorothioate deoxyguanosine oligomers. Immunopharmocology 29: 47-52.

Han, H. 2000. G-quadruplex DNA: a potential target for anti-cancer drug design. Trends Pharmacol. Sci. 21: 136-142.

Hanly, J. G., C. Hong, et al. (1995). "Immunomodulating effects of synchronised plasmapheresis and intravenous bolus cyclophosphamide in systemic lupus erythematosus." Lupus 4(6): 457-63.

Heijnen, C. J., K. H. Pot, et al. (1982). "Functional analysis of the defective T cell regulation of the antigen-specific PFC response in SLE patients: differentiation of suppressor precursor cells to suppressor effector cells." Clin Exp Immunol 47(2): 359-67.

Hemmi, H., O. Takeuchi, T. Kawai, et al. 2000. A Toll-like receptor recognizes bacterial DNA. Nature 408: 740-745.

Herscowitz, H. B., T. Sakane, et al. (1980). "Heterogeneity of human suppressor cells induced by concanavalin A as determined in simultaneous assays of immune function." J Immunol 124(3): 1403-10.

Homberg, J. C. (1984). "[Autoimmunity induced by drugs. Immunological characteristics and etiopathogenic hypotheses]." Presse Med 13(45): 2755-60.

Honda, M., T. Sakane, et al. (1982). "Studies of immune functions of patients with systemic lupus erythematosus: antibodies to desialized, rather than intact, T cells preferentially bind to and eliminate suppressor effector T cells." J Clin Invest 69(4): 940-9.

Horowitz, S., W. Borcherding, et al. (1977). "Induction of suppressor T cells in systemic lupus erythematosus by thymosin and cultured thymic epithelium." Science 197(4307): 999-1001.

Horwitz, D. A. and J. B. Cousar (1975). "A relationship between impaired cellular immunity humoral suppression of lymphocyte function and severity of systemic lupus erythematosus." Am J Med 58(6): 829-35.

Horwitz, D. A., J. D. Gray, et al. (2002). "The potential of human regulatory T cells generated ex vivo as a treatment for lupus and other chronic inflammatory diseases." Arthritis Res 4(4): 241-6.

Hsieh, K. H. (1980). "[Lymphocytes, lymphocyte subpopulations and diseases related to abnormalities of suppressor-cell function]." Zhonghua Min Guo Wei Sheng Wu Ji Mian Yi Xue Za Zhi 13(2): 209-28.

Ilfeld, D. N. and R. S. Krakauer (1980). "Suppression of immunoglobulin synthesis of systemic lupus erythematosus patients by concanavalin A-activated normal human spleen cell supernatants." Clin Immunol Immunopathol 17(2): 196-202.

Inghirami, G., J. Simon, et al. (1988). "Activated T lymphocytes in the peripheral blood of patients with systemic lupus erythematosus induce B cells to produce immunoglobulin." Clin Exp Rheumatol 6(3): 269-76.

Ito, S., M. Ueno, et al. (1992). "Suppression of spontaneous murine lupus by inducing graft-versus-host reaction with CD8+ cells." Clin Exp Immunol 90(2): 260-5.

In't Veld Bas A et al Nosteroidal Antiinflammory Drugs and the risk of Alzheimers Disease. New Eng J Med 345.211515-1521 2001.

Isomaki, P. et al. J. Immunol. 2001 166, 5495-5507.

Janeway C A Jr. The immune system evolved to discriminate infectious nonself from noninfectious self. Immunol Today 1992; 13:11-6.

Janeway C A Jr. Approaching the asymptote? Evolution and revolution in immunology. 1999 Cold Spring Harb Quant Biol. 54:11-13.

Janeway C A Jr. The immune system evolved to discriminate infectious non self from noninfectious self. 1992. Immol Today 13:11-16.

Jonuleit, H., E. Schmitt, M. Stassen, et al. 2001. Identification and functional characterization of human CD4(+) CD25(+) T cells with regulatory properties isolated from peripheral blood. J. Exp. Med. 193: 1285-1294.

Jonuleit, H., E. Schmitt, G. Schuler, et al. 2000. Induction of human IL-10-producing, non-proliferating CD+ T cells with regulatory properties by repetitive stimulation with allogeneic immature dendritic cells. J. Exp. Med. 192: 1213-1222.

Kaliyaperumal, A., M. A. Michaels, et al. (1999). "Antigen-specific therapy of murine lupus nephritis using nucleosomal peptides: tolerance spreading impairs pathogenic function of autoimmune T and B cells." J Immunol 162(10): 5775-83.

Kammer, G. M., R. E. Birch, et al. (1983). "Impaired immunoregulation in systemic lupus erythematosus: defective adenosine-induced suppressor T lymphocyte generation." J Immunol 130(4): 1706-12.

Kammer, G. M. 1999. High prevalence of T cell type I protein kinase A deficiency in systemic lupus erythematosus. Arthritis Rheum. 42: 1458-1465.

Kammer, G. M., et al. 1996. Deficient type I protein kinase A isozyme activity in systemic lupus erythematosus T lymphocytes. II. Abnormal isozyme kinetics. J. Immunol. 157: 2690-2698.

Kapusta, M. A. (1980). "The virus-activated suppressor cell hypothesis in experimental and human rheumatic diseases." J Rheumatol 7(3): 309-15.

Kartashova, V. I., O. V. Zairat'iants, et al. (1997). "[Thymus in systemic lupus erythematosus]." Klin Med (Mosk) 75(1): 24-6.

Kaufman, D. B. and E. Bostwick (1979). "Defective suppressor T-cell activity in systemic lupus erythematosus." Clin Immunol Immunopathol 13(1): 9-18.

Klinman, D. M., J. Conover & C. Coban. 1999. Repeated administration of synthetic oligodeoxynucleotides expressing CpG motifs provides long-term protection against bacterial infection. Infect. Immun. 67: 5658-5663.

Klinman, D. M., G. Yamshchikov & Y. Ishigatsubo. 1997. Contribution of CpG motifs to the immunogenicity of DNA vaccines. J. Immunol. 158: 3635-3642.

Klinman, D. M. & T. B. Nutman. 1994. ELIspot assay to detect cytokine-secreting murine and human cells. In Current Protocols in Immunology. J. E. Coligan, A. M. Kruisbeek, D. H. Margulies, et al, Eds. Greene Publishing Associates. Brooklyn, N.Y.

Klinman, D. M., A. Yi, S. L. Beaucage, et al. 1996. CpG motifs expressed by bacterial DNA rapidly induce lymphocytes to secrete IL-6, IL-1 2, and IFNg. Proc. Natl. Acad. Sci. USA 93: 2879-2883.

Klinman, D. M., D. Verthelyi, F. Takeshita & K. J. Ishii. 1999. Immune recognition of foreign DNA: a cure for bioterrorism? Immunity 11: 123-129.

Krieg, A. M., A. Yi, S. Matson, et al. 1995. CpG motifs in bacterial DNA trigger direct B-cell activation. Nature 374: 546-548.

Krieg, A. M., T. Wu, R. Weeratna, et al. 1998. Sequence motifs in adenoviral DNA block immune activation by stimuatory CpG motifs. Proc. Natl. Acad. Sci. 95: 12631-12636.

Krieg, A. M. 2000. The role of CpG motifs in innate immunity. Curr. Opin. Immunol. 12: 35-43.

Krieg, A. M., L. L. Homan, A. K. Yi & J. T. Harty. 1998. CpG DNA induces sustained IL-12 expression in vivo and resistance to Listeria monocytogenes challenge. J. Immunol. 161: 2428-2434.

Krieg A M. et al., 1998. Sequence motifs in adenoviral DNA block immune activation by stimulatory CpG motifs. Proc Natl Acad Sci USA. 95(21):12631-6.

Koide, J., M. Takano, et al. (1986). "Direct demonstration of immunoregulatory T-cell defects in patients with systemic lupus erythematosus." Scand J Immunol 23(4): 449-59.

Koide, J., T. Takeuchi, et al. (1987). "Defects of autologous mixed lymphocyte reaction-activated immunoregulatory T cells in patients with systemic lupus erythematosus." Scand J Immunol 26(4): 363-9.

Koriyama, K. K. and J. C. Daniels (1980). "In vitro effects of thymosin on T-cell subsets in systemic lupus erythematosus." J Immunopharmacol 2(3): 381-96.

Krakauer, R. S., J. D. Clough, et al. (1980). "Suppressor cell defect in SLE: relationship to native DNA binding." Clin Exp Immunol 40(1): 72-6.

Krakauer, R. S., J. D. Clough, et al. (1979). "Suppressor cell function defect in idiopathic systemic lupus erythematosus." Clin Immunol Immunopathol 14(3): 327-33.

Krakauer, R. S., W. Strober, et al. (1977). "Prevention of autoimmunity in experimental lupus erythematosus by soluble immune response suppressor." Science 196(4285): 56-9.

Kretz-Romel A, Rubin R L. Disruption of positive selection of thymocytes causes auotimmunity. 2000 Nature Med. 6, 298-305.

Kasakawa R, Tojo T, Miyaawaki S, et al. Preliminary diagnostic criteria for the classification of mixed connective tissue disease. 1987; in Mixed Connective Tissue Disease and Antinuclear Antibodies Kasakawa R, Sharp G C, Eds. Amsterdam, Excerpta Medica p. 41.

Kardestuncer T, Frumkin H. Systemic lupus erythematosus in relation to environmental pollution in an African-American community in North Georgia. Arch Environ Health 1997 March-April;52(2):85-90.

Kondo T, Cortese I, Markovic-Plese S, Wadinger K P, Carter C, Brown M, Leitman S, Martin R. Dendritic cells signal T cells in the absence of exogenous antigen. Nature Immunol. Online 2001 Sep. 17 DOI : 10.1038/ni1711.

Kondo, Takajuki et al. Dendritic cells signal T cells in the absence of exogenous antigen. Nature Immunology. 2001.

Kinter et al J Ex Med 2004 Aug. 2; 200(3):331-334.)

Kuntz, M. M., J. B. Innes, et al. (1979). "The cellular basis of the impaired autologous mixed lymphocyte reaction in patients with systemic lupus erythematosus." J Clin Invest 63(1): 151-3.

Lavastida, M. T., A. L. Goldstein, et al. (1981). "Thymosin administration in autoimmune disorders." Thymus 2(4-5): 287-95.

Lemire, J. (2000). "1,25-Dihydroxyvitamin D3—a hormone with immunomodulatory properties." Z Rheumatol 59 Suppl 1: 24-7.

Lenert, P., L. Stunz, A. K. Yi, et al. 2001. CpG stimulation of primary mouse B cells is blocked by inhibitory oligodeoxyribonucleotides at a site proximal to NF-kappaB activation. Antisense Nucleic Acid Drug Dev. 11: 247-256.

Levings, M. K., R. Sangregorio & M. G. Roncarolo. 2001. Human CD25(+) CD4(+) T regulatory cells suppress naive and memory T cell proliferation and can be expanded in vitro without loss of function. J. Exp. Med. 193: 1295-1302.

Levings, M. K., R. Sangregorio, F. Galbiati, et al. 2001. IFN-$\alpha$ and IL-10 induce the differentiation of human type 1 T regulatory cells. J. Immunol. 166: 5530-5539.

Liebling, M. R., C. Wong, et al. (1988). "Specific suppression of anti-DNA production in vitro." J Clin Immunol 8(5): 362-71.

Linker-Israeli, M., F. P. Quismorio, Jr., et al. (1990). "CD8+ lymphocytes from patients with systemic lupus erythematosus sustain, rather than suppress, spontaneous polyclonal IgG production and synergize with CD4+ cells to support autoantibody synthesis." Arthritis Rheum 33(8): 1216-25.

Lu, Q. & G. Lemke. 2001. Homeostatic regulation of the immune system by receptor tyrosine kinases of the Tyro 3 family. Science 293: 306-311.

Lanzavecchia, A. & F. Sallusto. 2001. Regulation of T cell immunity by dendritic cells. Cell 106: 263.

Mosmann, T. R. & R. L. Coffman. 1989. Th1 and Th2 cells: different patterns of lymphokine secretion lead to different functional properties. Annu. Rev. Immunol. 7: 145.

Mosmann, T. R. & S. Sad. 1996. The expanding universe of T-cell subsets: Th1, Th2 and more. Immunol. Today 17: 138-146.

Moutsopoulos H M, Tzioufas A G. Sjogrens Syndrome 1994 in Rheumatology Klippel J H, Dieppe P A. Eds. 6:27.1.

Mandell B F and Calabrese L Laboratory Testing and the Diagnosis of Selected Rheumatic Diseases p 13 in Rheumatic Diseases and the Environment Kaufman L D and Varga J Eds Arnold Publ. 1999.

Miller F W GENETICS OF Environmentally Associated Rheumatic Disease p 33-39 in Rheumatic Diseases and the Environment Kaufman L D and Varga J Eds Arnold Publ. 1999.

Maverakis, E., van den Elzen, P., and Sercarz, E. E. Self-reactive T cells and degeneracy of T cell recognition: evolving concepts from sequence homology to shape mimicry and TCR flexibility. Journal of Autoimmunity 2001 16: 201-209.

Mason D, Powrie F. Control of Immune Pathology by regulatory T cells Curr. Opin. Immunol. 1998; 10: 645-655.

Mevorach, D. et al. Complement-dependent clearance of apoptotic cells by human macrophages. J. Exp. Med. 1998. 188, 2313-2320.

Mosmann T R, Coffman R L. Establishment of the TH 1 and TH 2 paradigm: TH ! And TH 2 cells: different patterns of lymphokine. 1989. Ann. Rev. Immunol 7. 145-173.

McGeer et al. Anti-inflammatory drugs and Alzheimers Disease. Lancet 337.1426 1990.

Medzhitov R, Janeway C A Jr. Innate immunity: the virtues of a nonclonal system of recognition. Cell 1997; 91: 295-8.

Medzhitov R, Janeway C A Jr. Innate immunity. N Engl J Med 2000; 343:338-44.

Maloy, Kevin J. and Powrie, Fiona. Regulatory T cells in the control of immune pathology. Nature Immunology. 2001 2: 816-822.

Maloy K, Powrie P. Regulatory T cells in the control of immune pathology. Nature Immunology 2001; 2, 816-822.

Martinez F D The coming-of-age of the hygiene hypothesis. Respir. Res 2 129-132. 2001.

Matzinger P. Danger Model: A Renewed Sense of Self Science 296: 301-305 2002.

Matzinger P. Tolerance, Danger and the extended family. Ann Rev Immunol 1994 12:991-1045.

Matzinger P. An Innate sense of danger. Seminars in Immunology 1998 10:399-415.

Mach, P. S., M. Kharouby, et al. (1984). "The in vitro production and regulation of anti-double stranded DNA antibodies by peripheral blood mononuclear cells from normals and patients with systemic lupus erythematosus." Clin Exp Immunol 57(2): 338-44.

Markenson, J. A., M. D. Lockshin, et al. (1980). "Supressor monocytes in patients with systemic lupus erythematosus. Evidence of suppressor activity associated with a cell-free soluble product of monocytes." J Lab Clin Med 95(1): 40-8.

Markenson, J. A., J. W. Morgan, et al. (1978). "Responses of fractionated cells from patients with systemic lupus erythematosus and normals to plant mitogen: evidence for a suppressor population of monocytes." Proc Soc Exp Biol Med 158(1): 5-9.

Matzinger, P. & S. Guerder. 1989. Does T-cell tolerance require a dedicated antigen-presenting cell? Nature 338: 74-76.

Menges, M., S. Rossner, C. Voigtlander, et al. 2002. Repetitive injections of dendritic cells matured with tumor necrosis factor $_\alpha$ induce antigen-specific protection of mice from autoimmunity. J. Exp. Med. 195: 15-22.

Matsumoto, K. and M. Hatano (1984). "Defective cellular immune responses in lupus nephritis." J Clin Lab Immunol 14(3): 161-3.

Matsumoto, K., K. Osakabe, et al. (1984). "Defective concanavalin A-induced suppressor cell activity in lupus nephritis." Int Arch Allergy Appl Immunol 75(1): 48-51.

McInerney, M. F., J. D. Clough, et al. (1988). "Two distinct subsets of patients with systemic lupus erythematosus." Clin Immunol Immunopathol 49(1): 116-32.

Medzhitov, R. & C. A. Janeway. 1997. Innate immunity: the virtues of a nonclonal system of recognition. Cell 91: 295-298.

Mevorach, D., J. Mascarenhas, D. A. Gershov, et al. 1998. Complement-dependent clearance of apoptotic cells by human macrophages. J. Exp. Med. 188: 2313-2320.

Meroni, P. L., G. Balestrieri, et al. (1983). "Con A suppressor cell assay: a further characterization." J Clin Lab Immunol 10(3): 159-63.

Miller, H. C. and C. Vito (1989). "Action of a thymic cytokine TsIF in reversing the autoimmune disease state of the MRL/lpr mouse." Mol Biother 1(4): 213-7.

Miller, K. B. and D. Salem (1982). "Immune regulatory abnormalities produced by procainamide." Am J Med 73(4): 487-92.

Miller, K. B. and R. S. Schwartz (1979). "Familial abnormalities of suppressor-cell function in systemic lupus erythematosus." N Engl J Med 301(15): 803-9.

Morel, L., et al. 1994. Polygenic control of susceptibility to murine systemic lupus erythematosus. Immunity 1: 219-229.

Moretta, A., M. C. Mingari, et al. (1979). "Human T-lymphocyte subpopulations: alterations in systemic lupus erythematosus." Scand J Immunol 10(3): 223-8.

Morimoto, C. (1978). "Loss of suppressor T-lymphocyte function in patients with systemic lupus erythematosus (SLE)." Clin Exp Immunol 32(1): 125-33.

Morimoto, C., T. Abe, et al. (1979). "Altered function of suppressor T lymphocytes in patients with active systemic lupus erythematosus—in vitro immune response to autoantigen." Clin Immunol Immunopathol 13(2): 161-70.

Morimoto, C., T. Abe, et al. (1979). "Studies of anti-lymphocyte antibody of patients with active SLE. I. Cause of loss of suppressor T-lymphocyte function." Scand J Immunol 10(3): 213-21.

Morimoto, C., T. Abe, et al. (1980). "Studies of anti-lymphocyte antibody in patients with active SLE. II. Effect of anti-lymphocyte antibody on autoreactive cell clones." Scand J Immunol 11(5): 479-88.

Morimoto, C., N. L. Letvin, et al. (1985). "The isolation and characterization of the human suppressor inducer T cell subset." J Immunol 134(3): 1508-15.

Morimoto, C., E. L. Reinherz, et al. (1980). "Characteristics of anti-T-cell antibodies in systemic lupus erythematosus: evidence for selective reactivity with normal suppressor cells defined by monoclonal antibodies." Clin Immunol Immunopathol 16(4): 474-84.

Morimoto, C., E. L. Reinherz, et al. (1984). "Relationship between systemic lupus erythematosus T cell subsets, anti-T cell antibodies, and T cell functions." J Clin Invest 73(3): 689-700.

Morimoto, C., E. L. Reinherz, et al. (1980). "Alterations in immunoregulatory T cell subsets in active systemic lupus erythematosus." J Clin Invest 66(5): 1171-4.

Morimoto, C. and S. F. Schlossman (1987). "Antilymphocyte antibodies and systemic lupus erythematosus." Arthritis Rheum 30(2): 225-8.

Murchie, A. I. 1994. Tetraplex folding of telomere sequences & the inclusion of adenine bases. EMBO J. 13: 993-1001.

Murata, H. and J. Yata (1986). "Defect of suppressor cell induction in patients with juvenile rheumatoid arthritis." Asian Pac J Allergy Immunol 4(2): 95-9.

Muryoi, T., T. Sasaki, et al. (1989). "Impaired accessory cell function of monocytes in systemic lupus erythematosus." J Clin Lab Immunol 28(3): 123-8.

Naiki, M., Y. Imai, et al. (1985). "Establishment of a nucleoside-specific suppressor T cell line from SLE prone (NZB/NZW)F1 mice." J Immunol 135(2): 1080-5.

Napirei, M., H. Karsunky, B. Zevnik, et al. 2000. Features of systemic lupus erythematosus in DNAse 1-deficient mice. Nat. Genet. 25: 177-181.

Nathan, Carl and Muller, William A. Putting the brakes on innate immunity: a regulatory role for CD200? Nature Immunology. 2001 Vol 2, No. 1 17-19.

Newman, B., S. Blank, et al. (1979). "Lack of suppressor cell activity in systemic lupus erythematosus." Clin Immunol Immunopathol 13(2): 187-93.

Ng, W. F., P. J. Duggan, F. Ponchel, et al. 2001. Human CD4(+) CD25(+) cells: a naturally occurring population of regulatory T cells. Blood 98: 2736-2744.

Ochi, T., E. A. Goldings, et al. (1983). "Immunomodulatory effect of procainamide in man. Inhibition of human suppressor T-cell activity in vitro." J Clin Invest 71(1): 36-45.

Ogden, C. A., A. de Cathelineau, P. R. Hoffman, et al. 2002. C1q and mannose binding lectin engagement of cell surface calreticulin and CD91 initiates macropinocytosis and uptake of apoptotic cells. J. Exp. Med. 194: 781-795.

Palacios, R., D. Alarcon-Segovia, et al. (1981). "Human postthymic precursor cells in health and disease. II. Their loss and dysfunction in systemic lupus erythematosus and their partial correction with serum thymic factor." J Clin Lab Immunol 5(2): 71-80.

Parks C G, Conrad K, Cooper G S. Occupational exposure to crystalline silica and autoimmune disease. Environ Health Perspect 1999 October; 107 Suppl 5: 793-802.

Parks C S et al Occupational Exposure to Crystalline Silica and Risk of Systemic Lupus Erythematosus Arthritis & Rheum v 46 no 7 1840-1850 2002.

Pisetsky, D. S. 1997. Immunostimulatory DNA: a clear and present danger? Nat. Med. 3: 829-831.

Pisetsky, D. S., C. Reich, S. D. Crowley & M. D. Halpern. 1995. Immunological properties of bacterial DNA. Ann. N.Y. Acad. Sci. 772: 152-163.

Pu, Z., Lovitch, S. B., Bikoff, E. K. & Unanue, E. R. T cells distinguish MHC-peptide complexes formed in separate vesicles and edited by H2-DM. Immunity 20, 467-476 (2004).

Ramirez, F., R. B. Searles, et al. (1988). "Interactions of IgG from SLE patients with peripheral blood mononuclear cells and adherent cell populations." Rheumatol Int 8(1): 15-20.

Rea, T. H., A. C. Bakke, et al. (1984). "Peripheral blood T lymphocyte subsets in leprosy." Int J Lepr Other Mycobact Dis 52(3): 311-7.

Reimer G, Scheer U, Peters J M, Tan E M. Immunolocalization oand partial characterization of a nuclear autoantigen (PM-Scl) associated with polymyositis/sclerodrma overlap syndromes. 1986 J Immunol 137:3802-3808.

Rosen A, Casciola-Rosen L. Autoantigens as substrates for apoptotic proteases: implications for the pathogenesis of systemic disease. Cell Death Differ 1999 January;6(1):6-12.

Rosen A, Casciola-Rosen L. Clearing the way to mechanisms of auotimmunity. 2001 Nature Med. Jun. 7:6; 664-665.

Smith M A et al. Oxidative stress in Alzheimers disease. 2000 Biochimica et Biophysica Acta (BBA) Molecular Basis of Disease. 1502:139-144.

Sakaguchi, S. Animal models of autoimmunity and their relevance to human diseases. Curr Opin Immunol 2000 12, 684-690.

Robey, F. A., K. D. Jones, T. Tanaka, et al. 1984. Binding of C-reactive protein to chromatin and nucleosome core particles. J. Biol. Chem. 259: 7311-7316.

Rohowsky-Kochan, C., D. Eiman, et al. (1990). "Decreased suppressor-inducer T lymphocytes in multiple sclerosis and other neurological diseases." J Neuroimmunol 28(2): 161-6.

Rolink, A. G. and E. Gleichmann (1983). "Allosuppressor- and allohelper-T cells in acute and chronic graft-vs.-host (GVH) disease. III. Different Lyt subsets of donor T cells induce different pathological syndromes." J Exp Med 158(2): 546-58.

Rolink, A. G., S. T. Pals, et al. (1983). "Allosuppressor and allohelper T cells in acute and chronic graft-vs.-host disease. II. F1 recipients carrying mutations at H-2K and/or I-A." J Exp Med 157(2): 755-71.

Roman, M., E. Martin-Orozco, J. S. Goodman, et al. 1997. Immunostimulatory DNA sequences function as T helper-1 promoting adjuvants. Nat. Med. 3: 849-854.

Roncarolo, M. G., R. Bacchetta, C. Bordignon, et al. 2001. Type 1 T regulatory cells. Immunol. Rev. 182: 68-79.

Rosen A, Casciola-Rosen L, Wigley F. Role of Metal catalyzed oxidation reactions in the early pathogenesis of scleroderma. Current Opinion in Rheumatology 9:538-543 1997.

Sagawa, A. and N. I. Abdou (1979). "Suppressor-cell antibody in systemic lupus erythematosus. Possible mechanism for suppressor-cell dysfunction." J Clin Invest 63(3): 536-9.

Sakane, T., H. Kotani, et al. (1983). "A defect in the suppressor circuits among OKT4+ cell populations in patients with systemic lupus erythematosus occurs independently of a defect in the OKT8+ suppressor T cell function." J Immunol 131(2): 753-61.

Sakane, T., S. Takada, et al. (1986). "Deficiencies in suppressor T cell activity seen in patients with active systemic lupus erythematosus are due to the dilution of normally functioning suppressor T cells by nonsuppressor T cells." J Immunol 137(12): 3809-13.

Sansom, C. (1999). "Mice illuminate the pathways to lupus." Mol Med Today 5(12): 504-5.

Santambrogio, L. et al. Extracellular antigen processing and presentation by immature dendritic cells. Proc. Natl. Acad. Sci. USA 96, 15056-15061 (1999).

Sany, J. (1990). "[Pathogenic role of antinuclear antibodies in lupus disease]." Ann Med Interne (Paris) 141(3): 222-6.

Saoudi, A., B. Seddon, V. Heath, et al. 1996. The physiological role of regulatory T cells in the prevention of autoimmunity: the function of the thymus in the generation of the regulatory T cell subset. Immunol. Rev. 149: 195-216.

Sakaguchi, S. 2000. Regulatory T cells: key controllers of immunologic self-tolerance. Cell 101: 455-458.

Sakabe K, Yoshida T, Furuya H, Kayama F, Chan E K. Estrogenic xenobiotic increase expression of SS-A/Ro autoantigens in cultures human epidermal cells. Acta Derm Venerol 1998 November; 78(6): 420-423.

Scott R S, McMahon E J, Pop S M, Reap E A, Caricchio R, Cohen P, Earp S, & Matsushima G K. Phagocytosis and clearance of apoptotic cells is mediated by MER. Nature 2001 411,207-211.

Sharp G C, Irwin W, Tan E M et al Mixed Connective Tissue Disease—an apparently distinct rheumatic disease syndrome associated with a specific antibody to an extractable nuclear antigen (ENA) 1977 Am. J. Med 52:148-159.

Shero J H, Bordwell B, Rothfield N F, Earnshaw W C. Autoantibodies to topoismerse 1 are found in sera from scleroderma patients. 1986. Science 231:737-740.

Scott, J. R., N. S. Rote, et al. (1987). "Immunologic aspects of recurrent abortion and fetal death." Obstet Gynecol 70(4): 645-56.

Scott, R. S., E. J. McMahon, S. M. Pop, et al. 2001. Phagocytosis and clearance of apoptotic cells is mediated by mer. Nature 411: 207-211.

Segal, B. M., J. T. Chang & E. M. Shevach. 2000. CpG oligonucleotides are potent adjuvants for the activation of autoreactive encephalotogenic T cells in vivo. J. Immunol. 164: 5683-5688.

Sehgal, V. N., S. A. Wagh, et al. (1992). "Peripheral T lymphocytes and their subsets in cutaneous tuberculosis." Int J Dermatol 31(2): 110.

Shevach E M, Regulatory T cells in autoimmunity. Ann. Rev. Immunol 2000; 18: 423-449.

Shoenfeld, Y., M. Blank, et al. (1993). "Manipulation of autoimmune diseases with T-suppressor cells: lessons from experimental SLE and EAE." Immunol Lett 36(2): 109-16.

Singh, R. R., F. M. Ebling, et al. (2002). "Induction of autoantibody production is limited in nonautoimmune mice." J Immunol 169(1): 587-94.

Smith, C. I. and A. Svejgaard (1981). "Concanavalin-A-induced suppressor lymphocytes in normal individuals." Scand J Immunol 13(5): 483-92.

Smolen, J. S., S. O. Sharrow, et al. (1981). "The human autologous mixed lymphocyte reaction. I. Suppression by macrophages and T cells." J Immunol 127(5): 1987-93.

Smolen, J. S., K. Siminovitch, et al. (1983). "Responder cells in the human autologous mixed lymphocyte reaction (AMLR). Characterization and interactions in healthy individuals and patients with systemic lupus erythematosus." Behring Inst Mitt (72): 135-42.

Sobel, E. S., et al. 2002. The major murine systemic lupus erythematosus susceptibility locus Sle1 results in abnormal functions of both B and T cells. J. Immunol. 169: 2694-2700.

Sparwasser, T., E. Koch, R. M. Vabulas, et al. 1998. Bacterial DNA and immunostimulatory CpG oligonucleotides trigger maturation and activation of murine dendritic cells. Eur. J. Immunol. 28: 2045-2054.

Sparwasser, T., T. Meithke, G. Lipford, et al. 1997. Bacterial DNA causes septic shock. Nature 386: 336-338.

Steinman et al. 2003. Dendritic cell function in vivo during the steady state: a role in peripheral tolerance. Ann. N.Y. Acad. Sci. 987.

Steinman, R. M. & M. C. Nussenzweig. 2002. Avoiding horror autotoxicus: the importance of dendritic cells in peripheral T cell tolerance. Proc. Natl. Acad. Sci. USA 99: 351-358.

Steinman, R. M., S. Turley, I. Mellman, et al. 2000. The induction of tolerance by dendritic cells that have captured apoptotic cells. J. Exp. Med. 191: 411-416.

Stunz, L. L., P. Lenert, D. Peckham, et al. 2002. Inhibitory oligonucleotides specifically block effects of stimulatory CpG oligonucleotides in B cells. Eur. J. Immunol. 32:1212-1222.

Yamada, H., I. Gursel, F. Takeshita, et al. 2002. Effect of suppressive DNA on CpG-induced immune activation. J. Immunol. 169: 5590-5596.

Zeuner, R. A., K. J. Ishii, M. J Lizak, et al. 2002. Reduction of GpG-induced arthritis by suppressive oligodeoxynucleotides. Arthritis Rheum. 46: 2219-2224.

Tan E. Antibody Markers in Systemic Autoimmunity. Diagnostic Studies in Rheumato.logy Ciba Geigy Publisher Kenneth D. Brandt Ed. 1992.

Tan E M et al Antinuclear antigens (ANAs): Diagnostic and specific immune markers and clues towards the understanding of autoimmunity. 1988. Clin. Immunol. Immunopathol 47: 121-141.

Tan E M, Cohen A S, Fries J F et al The 1982 revised criteria for the classification of systemic lupus erythematosus Arthritis &Rheum. 1982; 25:1272-1277.

Taneja V, David C S. Lessons from animal models for human autoimmune diseases. Nature Immunology 2001; 2, 781-784.

Tervaert J W C, Stegman C A, Kallenberg C G M. Silicon Exposure and vasculitis. Current Opinion in Rheumatology 10: 12-17 1998.

Umetsu D et al Asthma: an epidemic of dysregulated immunity. Nat Immunol vol 3 no 8.715-720. 2002.

Van Dyke K The possible role of peroxynitrite in Alzheimers Disease: a simple hypothesis that could be tested more thoroughly 1997 Med Hypotheses May;48(5):375-80.

Voll R E Immunosuppressive effects of apoptotic cells. 1997. Nature 390, 350-351.

Watts R A, Scott D G I, and Lane S E Epidemiology of Wegeners Granulomatosis Microscopic Polyangiitis and Churg and Strauss Syndrome p 84 Cleveland Clinic J of Med. Supplement 2, vol 69. 2002.

Takeshita, F., C. A. Leifer, I. Gursel, et al. 2001. Cutting edge: role of toll-like receptor 9 in CpG DNA-induced activation of human cells. J. Immunol. 167: 3555-3558.

Takeshita, S., F. Takeshita, D. E. Haddad, et al. 2000. CpG oligodeoxynucleotides induce murine macrophages to up-regulate chemokine mRNA expression. Cell Immunol. 206: 101-106.

Theofilopoulos, A. N. & D. H. Kono. 1999. The genes of systemic autoimmunity. Proc. Assoc. Am. Physicians 111: 228-40.

Thomasset, M. (1994). "[Vitamin D and the immune system]." Pathol Biol (Paris) 42(2): 163-72.

Tsokos, G. C. 1992. Lymphocyte abnormalities in human lupus. Clin. Immunol Immunopathol. 63: 7-9.

Twomey, J. J., A. H. Laughter, et al. (1978). "A serum inhibitor of immune regulation in patients with systemic lupus erythematosus." J Clin Invest 62(3): 713-5.

Via, C. S., S. O. Sharrow, et al. (1987). "Role of cytotoxic T lymphocytes in the prevention of lupus-like disease occurring in a murine model of graft-vs-host disease." J Immunol 139(6): 1840-9.

Via, C. S. and G. M. Shearer (1988). "Functional heterogeneity of L3T4+ T cells in MRL-lpr/lpr mice. L3T4+ T cells suppress major histocompatibility complex-self-restricted L3T4+ T helper cell function in association with autoimmunity." J Exp Med 168(6): 2165-81.

Volkmann, A., T. Zal & B. Stockinger. 1997. Antigen-presenting cells in thymus that can negatively select MHC class II-restricted T cells recognizing a circulating self antigen. J. Immunol. 158: 693-706.

Warrington, R. J. and W. J. Rutherford (1990). "Normal mitogen-induced suppression of the interleukin-6 (IL-6) response and its deficiency in systemic lupus erythematosus." J Clin Immunol 10(1): 52-60.

Wollina, U. (1984). "Immune complexes—pathogenetic factors of autoimmune systemic lupus erythematosus."Allerg Immunol (Leipz) 30(1): 3-13.

Xu, Y. and P. H. Wiernik (2001). "Systemic lupus erythematosus and B-cell hematologic neoplasm." Lupus 10(12): 841-50.

Yajima, K., A. Nakamura, et al. (2003). "FcgammaRIIB deficiency with Fas mutation is sufficient for the development of systemic autoimmune disease." Eur J Immunol 33(4): 1020-9.

Yamamoto, S., T. Yamamoto, T. Katoaka, et al. 1992. Unique palindromic sequences in synthetic oligonucleotides are required to induce IFN and augment IFN-mediated natural killer activity. J. Immunol. 148: 4072-4076.

Yamaguchi, H., M. Fukuzaki, et al. (1989). "[Graves' disease complicated with systemic lupus erythematosus (SLE): a case report]." Fukuoka Igaku Zasshi 80(7): 385-90.

Yasutomo, K., T. Horiuchi, S. Kagami, et al. 2001. Mutation of DNAse1 in people with systemic lupus erythematosus. Nat. Genet. 28: 313-314.

Young, M. C., J. D. Bangs, et al. (1981). "Immune suppression to nucleosides: differences between NZB and NZW mice." Eur J Immunol 11(5): 424-8.

Walker, P. S., T. Scharton-Kersten, A. M. Krieg, et al. 1999. Immunostimulatory oligodeoxynucleotides promote protective immunity and provide systemic therapy for leishmaniasis via IL-12 and IFNg dependent mechanisms. Proc. Natl. Acad. Sci. USA 96: 6970-6975.

Walport, M. J., et al. 1997. Complement deficiency and autoimmunity. Ann. N.Y. Acad. Sci. 815: 267-281.

Weigle, W. O. Analysis of autoimmunity through experimental models of thyroiditis and allergic encephalomyelitis. Adv Immunol 1980 30:159-273.

Wucherpfennig, K. W. Structural basis of molecular mimicry. Journal of Autoimmunity 2001 16: 293-302.

Zhao, H., S. H. Cheng & N. S. Yew. 2000. Requirements for effective inhibition of immunostimulatory CpG motifs by neutralizing motifs. Antisense Nucleic Acid Drug Dev. 10: 381-389.

Zimmermann, S., O. Egeter, S. Hausmann, et al. 1998. CpG oligodeoxynucleotides trigger protective and curative Th1 responses in lethal murine leishmaniasis. J. Immunol. 160: 3627-3630.

---

Having thus described our invention, what I claim as new, and desire to secure by Letters Patent is:

1. A vaccine composition for treating inflammatory, non infectious and/or post infectious, allergic, autoimmune, vasculitic, degenerative vascular, host v graft, graft v host diseases, Alzheimer's Disease, and amyloidosis comprising:
   a suppressor-regulator T cell activating amount of a synthetic, methylated DNA sequence of about 10 k to about 50 k Daltons, containing at least one SEQ ID NO 1 sequence and at least one SEQ ID NO 2 sequence.

2. The vaccine composition, according to claim 1, wherein said DNA is double-stranded.

3. The vaccine composition, according to claim 1, further comprising at least one agent selected from the group consisting of cytokines, antibodies, anti-TNF.alpha. biologics, and immunosuppressive agents.

4. The vaccine composition, according to claim 3, wherein said cytokine is chosen from the group consisting of IL-10 and TGF.beta.

5. The vaccine composition, according to claim 3, wherein said anti-TNF.alpha. biologics are chosen from the group consisting of Etanercept/Enbrel, Infliximab/Remicade, and Humira.

6. The vaccine composition, according to claim 3, wherein said immunosuppressive agent is chosen from the group consisting of Corticosteroids, Methotrexate, Bromocriptine, Immuran Cellcept, and vitamin D analogues.

7. A vaccine comprising: a suppressor-regulator T cell activating amount of a synthetic DNA molecule, said DNA molecule further comprising:
   At least one methylated region;
   at least one SEQ ID NO 1 sequence; and
   at least one SEQ ID NO 2 sequence.

* * * * *